United States Patent
Basavanna et al.

(10) Patent No.: US 11,859,173 B2
(45) Date of Patent: Jan. 2, 2024

(54) ROBUST SELF-REGENERATABLE STIFF LIVING MATERIALS

(71) Applicants: Northeastern University, Boston, MA (US); President and Fellows of Harvard College, Cambridge, MA (US)

(72) Inventors: Avinash M. Basavanna, Allston, MA (US); Anna Duraj-Thatte, Kensington, CA (US); Neel S. Joshi, Somerville, MA (US)

(73) Assignees: Northeastern University, Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 17/366,757

(22) Filed: Jul. 2, 2021

(65) Prior Publication Data
US 2022/0025319 A1    Jan. 27, 2022

Related U.S. Application Data

(60) Provisional application No. 63/047,615, filed on Jul. 2, 2020.

(51) Int. Cl.
*C12N 1/20* (2006.01)
*C12N 1/18* (2006.01)
*C12R 1/19* (2006.01)

(52) U.S. Cl.
CPC ............. *C12N 1/20* (2013.01); *C12N 1/18* (2013.01); *C12R 2001/19* (2021.05)

(58) Field of Classification Search
CPC ........ C12N 1/20; C12N 1/18; C12R 2001/19; C12R 2001/225; C12R 2001/865
See application file for complete search history.

(56) References Cited

PUBLICATIONS

Liu, Xinyue, et al. "3D printing of living responsive materials and devices." Advanced Materials 30.4 (2018): 1704821. (Year: 2017).*
Retegi, A., et al. "Bacterial cellulose films with controlled microstructure-mechanical property relationships." Cellulose 17.3 (2010): 661-669. (Year: 2010).*
Nguyen, Peter Q., et al. "Programmable biofilm-based materials from engineered curli nanofibres." Nature communications 5.1 (2014): 1-10. (Year: 2014).*
Drachuk, Irina, et al. "Immobilization of recombinant E. coli cells in a bacterial cellulose-silk composite matrix to preserve biological function." ACS Biomaterials Science & Engineering 3.10 (2017): 2278-2292. (Year: 2017).*
González, Lina M., Nikita Mukhitov, and Christopher A. Voigt. "Resilient living materials built by printing bacterial spores." Nature chemical biology 16.2 (2020): 126-133. (Year: 2020).*

(Continued)

*Primary Examiner* — Lora E Barnhart Driscoll
*Assistant Examiner* — Candice Lee Swift
(74) *Attorney, Agent, or Firm* — Foley Hoag LLP

(57) ABSTRACT

Disclosed are biomaterials, including engineered living materials (ELMs), comprising a plurality of microbial cells, wherein the material has a Young's Modulus of at least 5 Gpa; and methods of fabricating said biomaterials.

15 Claims, 30 Drawing Sheets

(56) References Cited

PUBLICATIONS

The Gund Company; https://thegundcompany.com/understanding-tensile-strength#:~:text=Ultimate%20tensile%20strength%20(UTS)%2C,stretched%20or%20pulled%20before%20breaking.; accessed Dec. 2, 2022 (Year: 2021).*

Rintahaka, Johanna, et al. "Phenotypical analysis of the Lactobacillus rhamnosus GG fimbrial spaFED operon: surface expression and functional characterization of recombinant SpaFED pili in Lactococcus lactis." PLoS One 9.11 (2014): e113922. (Year: 2014).*

* cited by examiner

Exploded View of Mold

EC-SLM

LR-SLM

SC-SLM

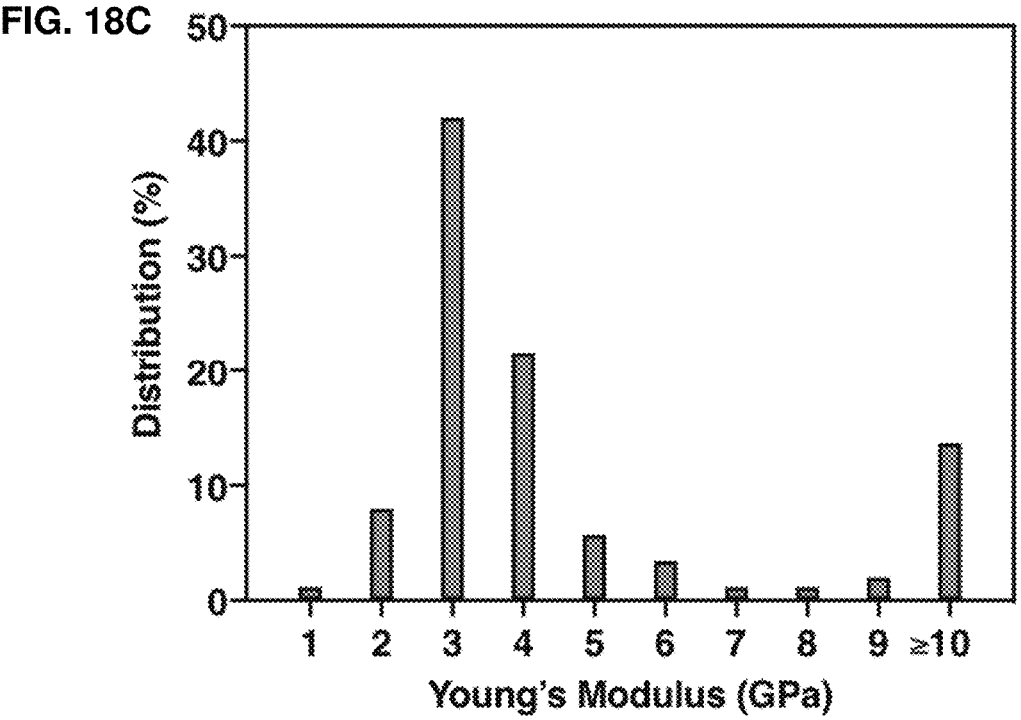

Gen I

Gen II

Gen III

ROBUST SELF-REGENERATABLE STIFF LIVING MATERIALS

RELATED APPLICATION

This application claims the benefit of priority to U.S. Provisional Application No. 63/047,615, filed on Jul. 2, 2020.

FIELD

The invention describes a method to fabricate Stiff Living Materials (SLMs). The materials are the first of their kind, wherein living microbial cells are utilized to make materials that are as strong and stiff as plastics, wood, bone and/or concrete. The SLMs also comprise living cells, which can be utilized to self-regenerate the materials. SLMs are resistant to organic solvents, like hexane, chloroform, acetonitrile, ethyl acetate, ethanol, methanol and dimethylformamide.

BACKGROUND

Advancements in materials and technology have played crucial roles in shaping the course of human evolution.(1) The present-day world showcases innumerable materials with remarkable properties. Such materials have enabled our way of life, but rarely account for the anthropogenic effects due to their make-use-dispose practices.(2) This unsustainable, linear material economy is in contrast to Nature's circular economy model that involves either regeneration or degradation at the end of the material's life cycle. Moreover, human-made materials are generally considered the result of "heat, beat, and treat" processes. This is due to their energy-intensive, high temperature/pressure and harsh chemical treatments, whereas biomaterials may be fabricated at ambient conditions from abundantly available benign components.(3-6) Thus, drawing inspirations from nature and harnessing the unparalleled manufacturing capabilities restored in living cells could lead to the development of an ultimate materials technology for a sustainable world.

In the last few decades, living cells have been meticulously engineered to produce a wide variety of small molecules, polymers, drugs and fuels.(7) Recently, cells have also been engineered to produce and/or modulate the properties or materials, which has led to the emergence of a new field known as engineered living materials (ELMs).(8-11) Primitive examples of ELMs have demonstrate binding to synthetic materials (e.g., stainless steel), templating nanoparticles (e.g., gold) and immobilizing enzymes (e.g., amylase).(12, 13) Subsequent ELMs that can function as catalytic surfaces, filtration membranes, under-water adhesives, pressure sensors, conductive films, gut adhesives and others, have been realized.(14-27) In spite of the impressive progress of ELMs, the living cells are predominantly employed as a foundry to produce materials and are seldom utilized for their unique characteristics like self-regeneration, self-regulation, self-healing, environmental responsiveness and self-sustainability. Incorporating any of these life-like characteristics into a robust living material has been a daunting task, which needs to be overcome with innovative strategies to further advance living materials technology.

SUMMARY

The present disclosure describes the use of soft living cells, such as microbial cells, to produce stiff and strong materials. Thus, in some aspects of the invention, disclosed herein are engineered living material (ELMs). In some embodiments, said ELMs comprise a plurality of microbial cells, wherein the ELMs have a Young's Modulus of at least 5 Gpa. In some aspects of the invention, provided herein are method of fabricating ELMs, wherein said ELMs have a Young's Modulus of at least 5 Gpa. Such methods may comprise proliferating a plurality of engineered xerotolerant microbial cells to produce a population of engineered living xerotolerant microbial cells; isolating and casting said living xerotolerant microbial cells onto a substrate; and allowing the isolated cells to dry; thereby forming an ELM.

In certain aspects of the invention, disclosed herein are engineered biomaterials, comprising a plurality of microbial cells. In some embodiments, the contemplated biomaterials have a Young's Modulus of at least 5 Gpa. In some such embodiments, the biomaterials do not comprise extracellular components. In some embodiments, the contemplated biomaterials do not comprise living microbial cells. In some aspects of the invention, provided herein are methods of fabricating a biomaterial, wherein the biomaterial has a Young's Modulus of at least 5 Gpa. The disclosed methods may comprise proliferating a plurality of engineered xerotolerant microbial cells to produce a population of engineered living xerotolerant microbial cells; isolating and casting said living xerotolerant microbial cells onto a substrate; and desiccating the isolated cells; thereby forming the biomaterial.

BRIEF DESCRIPTION OF THE DRAWINGS

FIGS. 18(A)-18(C) show nanoindentation analysis of SLM obtained from 70% ethanol treated *E. coli*. (A) Young's modulus, (B) Hardness and (C) Percentage distribution of Young's modulus shown in (A). The graphs show median and the range. Herein, the Young's modulus value was counted as "n" for any values within n±0.5, while that above 10 Gpa were also included with 10±0.5.

DETAILED DESCRIPTION

Figure 1A:
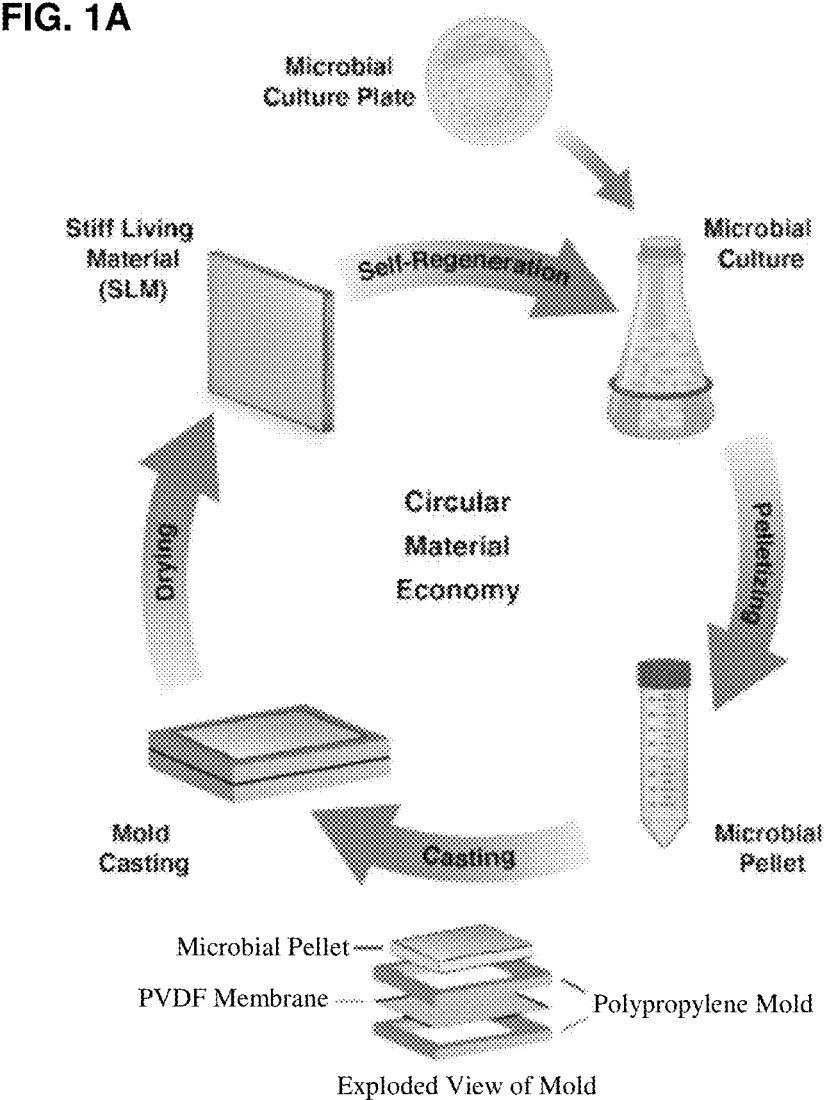
FIGS. 1(A)-1(F) illustrate the fabrication of stiff living materials (SLMs). (A) is a schematic showing the various stages involved in the fabrication of SLMs produced solely from microbial cells. The self-regeneration capability of SLMs results in a circular material economy. (PVDF=Polyvinylidene fluoride). Optical images of SLM fabricated at 25° C. and 40±5% relative humidity by air-drying for 24 h from (B) *Escherichia coli* (EC); (C) *Lactobacillus rhamnosus* (LR) and (D) *Saccharomyces cerevisiae* (SC) are shown. (Scale bar 0.5 cm.) (E) depicts Colony forming unit (CFU) counts of SLMs and their microbial pellet. (F) depicts percentage of live and dead cells estimated from the SLMs with respect to their pellet (dry weight corrected).

The present disclosure relates, at least in part, to living materials fabricated solely from microbial cells at ambient conditions that are stiff, strong and can self-regenerate. Living systems have not only the exemplary capability to fabricate materials (e.g. skin, wood, bone) at ambient conditions but also consist of living cells that enable them properties like growth and self-regeneration. In some aspects of the invention, disclosed herein is the fabrication of stiff living materials (SLMs) produced entirely from microbial cells without the incorporation of any structural biopolymers (e.g., cellulose, chitin, or collagen) or biominerals (e.g., hydroxyapatite, calcium carbonate) that are known to impart stiffness to biological materials. Notably, such SLMs are also lightweight, strong, resistant to organic solvents, and can self-regenerate. The living materials technology disclosed herein can serve as a powerful bio-manufacturing platform to design and develop sustainable structural materials, biosensors, self-regulators, self-healing, and environment-responsive smart materials. In this light, disclosed herein is the fabrication of the stiffest living materials to date, which can also self-regenerate, thereby serving as a unique example of circular material economy (FIG. 1A).

Most of the biomaterials (e.g., wood, silk) found in nature are formed at ambient conditions and degrade naturally to enable a sustainable eco-system. In contrast, the production of human-made materials (e.g., cement, plastics) require high temperatures or harsh chemical treatments, while their non-biodegradability unfavorably affects the environment. With the growing concerns on the global climate changes, there is an ever-increasing need to design materials for a sustainable world. This sustainability issue can be addressed by employing living cells as factories to produce materials at ambient conditions. Herein, living microbial cells, soft living cells, are utilized to produce stiff and strong materials.
Advantages Include:

Unlike, typical human-made materials that follow linear material economy (make-use-dispose practices), SLMs represent a unique example of a circular material economy. SLMs are not only biodegradable but can also regenerate. SLMs may be as stiff and strong as plastics, wood, bone. SLMs may be resistant to organic solvents.

In some embodiments, SLMs can harness the unique features of living cells such as self-regeneration, self-healing, self-regulation and environmental responsiveness. SLMs may be fabricated at room temperature without using any harmful chemicals. SLMs are cheap and easy to manufacture. SLMs comprise of benign cellular components and thereby offer sustainable solutions.
Potential Uses Include:

Provided herein are stiff and strong materials, solvent-resistant materials, self-regenerating materials, and methods of making said materials. The technology disclosed herein provides materials that have stiffness and strength similar to plastics, wood, silk, bone and concrete. In some aspects, the invention provides limitless opportunities to design and develop sustainable structural materials, biosensors, self-regulators, self-healing and environment-responsive smart materials. Also provided herein is basis (e.g., a platform) for future materials manufacturing technologies that inevitably rely on living cells.
Cost Advantages Include:

SLM may be fabricated from living microbial cells that can be grown at large-scale in bioreactors very easily and cheaply. SLM may be fabricated at room temperature by ambient drying and therefore do not involve any expensive processes. SLM can also regenerate.
Performance Advantages Include:

SLM falls into the circular material economy model, as they can self-regenerate and biodegrade completely under all environmental conditions. Living microbial cells are employed as factories to produce the material, thus the invention disclosed herein provides scalability and ease of fabrication.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

The term "extremophile" as disclosed herein refers to a microorganism (i.e., microbial cell) that exhibits optimal growth under extreme environment conditions. Extremophiles include acidophiles, alkaliphiles, halophiles, thermophiles, metalotolerant organisms, osmophiles, and xerophiles.

The terms "microbial cell," "microorganism," and "microbe" are used interchangeably and should be interpreted to encompass microscopic organism, particularly those commonly studied by microbiologists. Such organisms may include, but are not limited to, bacteria, fungi, and other single-celled organisms including the non-limiting examples of archaea, protozoa, fungi, algae, green algae, rotifers, planarians, and parasitic pathogens. Preferably, the microbes may be bacteria.

As used herein, the term "engineered microbial cell," "engineered microorganism," and "engineered microbe" refer to a microbial cell that has been genetically modified from its native state. For instance, an engineered microbial cell may have nucleotide insertions, nucleotide deletions, nucleotide rearrangements, and nucleotide modifications introduced into their DNA. These genetic modifications may be stably incorporated into the genome of the microbe (e.g., present in the chromosome of a bacteria or bacterial cell), or on an exogenous nucleic acid, such as a plasmid in a bacteria or bacterial cell. Accordingly, engineered microbial cells of the disclosure may comprise exogenous nucleotide sequences on plasmids. Alternatively, recombinant microbial cells may comprise exogenous nucleotide sequences stably incorporated into their genome. In some embodiments, the engineered microbe is non-pathogenic. In some embodiments, the engineered microbe is pathogenic. As used herein, the term "expression" refers to the transcription and stable accumulation of sense (mRNA) or anti-sense RNA derived from a nucleic acid, to translation of an mRNA into a polypeptide, and/or the final product encoded by a gene or fragment thereof.

The term "genetic modification," as used herein, refers to any genetic change. Exemplary genetic modifications include those that increase, decrease, or abolish the expression of a gene, including, for example, modifications of native chromosomal or extrachromosomal genetic material. Exemplary genetic modifications also include the introduction of at least one plasmid, modification, mutation, base deletion, base addition, and/or codon modification of chromosomal or extrachromosomal genetic sequence(s), gene over-expression, gene amplification, gene suppression, promoter modification or substitution, gene addition (either single or multi-copy), antisense expression or suppression, or any other change to the genetic elements of a host cell, whether the change produces a change in phenotype or not. Genetic modification can include the introduction of a plasmid, e.g., a plasmid comprising at least one amino acid catabolism enzyme operably linked to a promoter, into a bacterial cell. Genetic modification can also involve a targeted replacement in the chromosome, e.g., to replace a native gene promoter with an inducible promoter, regulated promoter, strong promoter, or constitutive promoter. Genetic modification can also involve gene amplification, e.g., introduction of at least one additional copy of a native gene into the chromosome of the cell. Alternatively, chromosomal genetic modification can involve a genetic mutation.

In some aspects of the invention, disclosed herein are engineered living material (ELMs). In some embodiments, said ELMs comprise a plurality of microbial cells, wherein the ELMs have a Young's Modulus of at least 5 Gpa. In some embodiments, the disclosed ELM has a Young's Modulus of at least 5 Gpa to 42 Gpa. In some embodiments, the ELM has a hardness of at least 0.2 Gpa to 2.4 Gpa. In certain embodiments, the ELM has a yield strength of at least 60-800 MPa.

Preferably, the ELMs disclosed herein consist essentially of microbial cells. Most preferably, said ELMs consist of microbial cells. Said microbial cells may be prokaryotic or eukaryotic. In some embodiments, the microbial cells are bacterial or fungal cells. In some embodiments, the microbial cells are *Escherichia coli, Lactobacillus rhamnosus*, or *Saccharomyces cerevisiae*. In certain embodiments, the microbial cells are engineered to be incapable of producing extracellular components. In some such embodiments, the microbial cells are *Escherichia coli* strain PQN4. The ELMs disclosed herein may comprise microbial cells which are xerotolerant. In some embodiments, the microbial cells are engineered to have enhanced xerotolerance. In certain embodiments, the microbial cells are extremophilic. In some embodiments, the microbial cells are a xerophilic.

In some embodiments, The ELMs disclosed herein comprise an outer surface of lysed and/or desiccated cells; and a core of living cells. Said core of living cells may have a planar packing density of at least 5-7 cells. In some embodiments, the core of living cells has a planar packing density of at least 6 cells. In some embodiments, the cells in the core of living cells die at an exponential rate. In some such embodiments, the core of living cells has a calculated cell death rate of less than 1 cell per day or less than 0.5 cells per day. Preferably, the core of living cells has a calculated cell death rate of about 0.43 cells per day.

In some embodiments, the ELMs disclosed herein are capable of self-regeneration. In other embodiments, the ELMs may be fully desiccated; and do not comprise living cells. In some embodiments, said ELMs are resistant to organic solvents.

In some aspects of the invention, provided herein are method of fabricating ELMs, wherein said ELMs have a Young's Modulus of at least 5 Gpa. Such methods may comprise proliferating a plurality of engineered xerotolerant microbial cells to produce a population of engineered living xerotolerant microbial cells; isolating and casting said living xerotolerant microbial cells onto a substrate; and allowing the isolated cells to dry; thereby forming an ELM. Said microbial cells may be prokaryotic or eukaryotic. In some embodiments, the microbial cells are bacterial or fungal cells. In some embodiments, the microbial cells are *Escherichia coli, Lactobacillus rhamnosus*, or *Saccharomyces cerevisiae*. In certain embodiments, the microbial cells are engineered to be incapable of producing extracellular components. In some such embodiments, the microbial cells are *Escherichia coli* strain PQN4. The ELMs disclosed herein may be fabricated from microbial cells engineered to have enhanced xerotolerance. In certain embodiments, the microbial cells are extremophilic. In some embodiments, the microbial cells are a xerophilic.

In some such embodiments of the invention, the substrate is porous. In preferred embodiments, the substrate comprises polyvinylidene fluoride (PVDF).

In some embodiments, the isolated cells are dried at 25° C. for up to 24 hours. Said isolated cells may be drawn down onto the substrate by applying vacuum suction. The dried living material may be removed from the substrate using an organic solvent, preferably dimethylformamide (DMF).

In some embodiments, the ELM comprises an outer surface of lysed and/or desiccated cells; and a core of living cells. The core of living cells has a planar packing density of at least 5-7 cells. Preferably, the core of living cells has a planar packing density of at least 6 cells. In some embodiments, the core of living cells has a cell death rate of less than 1 cell per day or less than 0.5 cells per day. Preferably, the core of living cells has a cell death rate of about 0.43 cells per day. In some embodiments, said ELM is capable of self-regeneration. In some such embodiments, said ELM is resistant to organic solvents.

In certain aspects of the invention, disclosed herein are engineered biomaterials, comprising a plurality of microbial cells. In some embodiments, the contemplated biomaterials have a Young's Modulus of at least 5 Gpa. In some such embodiments, the biomaterial does not comprise extracellular components. In some embodiments, the contemplated biomaterials do not comprise living microbial cells. In some embodiments, the biomaterial has a Young's Modulus of 5 Gpa to 42 Gpa. In some embodiments, the biomaterial has a hardness of 0.2 Gpa to 2.4 Gpa. In some embodiments, the biomaterial has a yield strength of 60-800 MPa.

The biomaterials contemplated herein may consist essentially of microbial cells. In other embodiments, the biomaterial consists of microbial cells. In some such embodiments, the microbial cells are prokaryotic or eukaryotic. In some embodiments, the microbial cells are bacterial or fungal cells. In some such embodiments, the microbial cells are *Escherichia coli, Lactobacillus rhamnosus*, or *Saccharomyces cerevisiae*. The microbial cells of the biomaterial may be engineered to be incapable of producing extracellular components. In some embodiments, the microbial cells are *Escherichia coli* strain PQN4. In some embodiments, the microbial cells are xerotolerant. In some embodiments, the microbial cells are engineered to have enhanced xerotolerance. The microbial cells may be extremophilic. In some embodiments, the microbial cells are xerophilic.

In some embodiments, the biomaterial disclosed herein may comprise an outer surface of lysed and/or desiccated microbial cells; and a core of intact desiccated microbial cells. In some such embodiments, the core of intact desiccated microbial cells may have a planar packing density of at least 5-7 cells. In some embodiments, core of intact desiccated microbial cells has a planar packing density of at least 6 cells. In other embodiments, the outer surfaces of the biomaterial comprises an array of desiccated intact microbial cells; and an amorphous core comprising lysed and/or desiccated cells.

In some embodiments, biomaterial is resistant to organic solvents.

In some aspects of the invention, provided herein are methods of fabricating a biomaterial, wherein the biomaterial has a Young's Modulus of at least 5 Gpa. The disclosed methods may comprise proliferating a plurality of engineered xerotolerant microbial cells to produce a population of engineered living xerotolerant microbial cells; isolating and casting said living xerotolerant microbial cells onto a substrate; and desiccating the isolated cells; thereby forming the biomaterial. Said microbial cells may be prokaryotic or eukaryotic. In some embodiments, the microbial cells are bacterial or fungal cells. In some embodiments, the microbial cells are *Escherichia coli, Lactobacillus rhamnosus*, or *Saccharomyces cerevisiae*. In certain embodiments, the microbial cells are engineered to be incapable of producing extracellular components. In some such embodiments, the microbial cells are *Escherichia coli* strain PQN4. The biomaterials disclosed herein may be fabricated from microbial cells engineered to have enhanced xerotolerance. In certain embodiments, the microbial cells are extremophilic. In some embodiments, the microbial cells are a xerophilic. In some such embodiments of the invention, the substrate is porous. In preferred embodiments, the substrate comprises polyvinylidene fluoride (PVDF). In some embodiments, the methods disclosed herein may further comprise applying vacuum suction to draw down the isolated cells onto the substrate. In some embodiments, the methods further comprise removing from the substrate desiccated biomaterial using an organic solvent, preferably dimethylformamide (DMF).

In some embodiments, the fabricated biomaterial comprises an outer surface of lysed and/or desiccated cells; and a core of intact desiccated cells. The core of intact desiccated cells may have a planar packing density of at least 5-7 cells. The core of intact desiccated cells may have a planar packing density of at least 6 cells.

In other embodiments, the outer surface of the fabricated biomaterial comprises an array of desiccated intact microbial cells; and an amorphous core comprising lysed and/or desiccated cells.

In some embodiments, said biomaterials are resistant to organic solvents.

Definitions of common terms in cell biology and molecular biology can be found in The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); and Current Protocols in Protein Science (CPPS) (John E. Coligan, et. al., ed., John Wiley and Sons, Inc.), which are all incorporated by reference herein in their entireties.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The following examples are set forth as being representative of the present disclosure. These examples are not to be construed as limiting the scope of the present disclosure as these and other equivalent embodiments will be apparent in view of the present disclosure, figures and accompanying claims.

Example 1: Materials and Methods

Figure 2A:
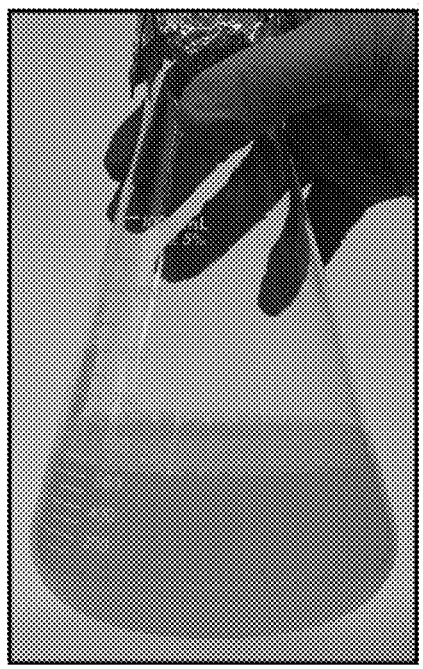
FIGS. 2(A)-2(C) show optical images of microbial culture and pellet. (A) *E. coli* culture in lysogeny broth after 24 h. (B) *E. coli* cells pelletized from the culture. (C) *E. coli* pellet after washing with deionized water.
Figure 2B:
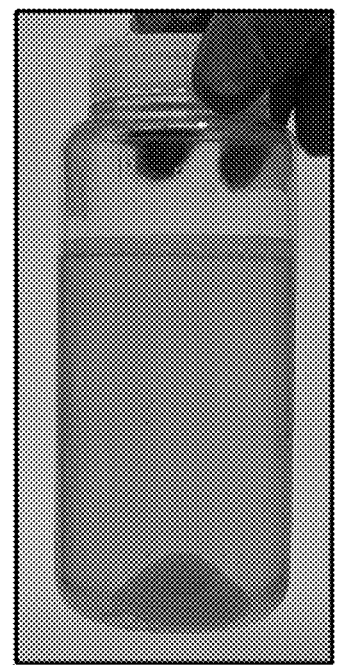
Figure 2C:
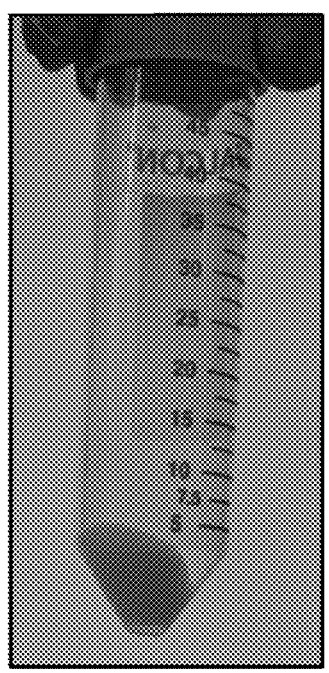

Cell Strains and Plasmids
SLMs were fabricated from the following cell strains;
PQN4, *Escherichia coli* cell strain derived from LSR10 (MC4100, ΔcsgA, λ(DE3), Cam$^R$). pET-21d(+) plasmid (Novagen 67743-3) was transformed to PQN4 to get ampicillin resistance.
*Lactobacillus rhamnosus* (ATCC® 27773™)
*Saccharomyces cerevisiae* (ATCC® 9763™)
Fabrication of SLMs
*E. coli* (lysogeny broth with carbenicillin, 37° C., 24 h), *L. rhamnosus* (MRS broth with chloramphenicol, 37° C., 48 h) and *S. cerevisiae* (YPD broth, 30° C., 24 h) were cultured (500 ml media) in an incubator. *E. coli* and *S. cerevisiae* cells were pelletized at 3000 rpm, whereas 8000 rpm was employed for *L. rhamnosus*. The microbial cells were then washed twice (250 ml and 50 ml) with milli-Q water to remove the culture media. (FIG. 2) The resulting microbial pellet was casted on a PVDF (polyvinylidene fluoride; Millipore Immobilon-P, IPVH09120) membrane, which was firmly sandwiched between polypropylene molds (inner dimensions 2 cm×2 cm×1.6 mm) by adhesive tapes. The microbial pellet was air-dried at ambient conditions (25° C. & 40±5% relative humidity) for 24 h. PVDF membrane strongly adheres to EC-SLM and LR-SLM, but did not stick to SC-SLM. By gently wiping the PVDF membrane with DMF (dimethylformamide) solvent and after 5-10 min, it can be easily peeled off. The SLMs were stored at ambient conditions and used as needed.
Colony Forming Unit (CFU) Analysis of SLMs 5-10 mg of SLM or 20-100 mg of the microbial pellet (water washed) was subjected to serial dilutions and each dilution was plated onto a selective agar plate. The resulting colonies were counted to obtain the CFU count. For time-dependent CFU analysis, the SLMs stored at ambient conditions were utilized at day 0, 15 and 30.
Thermal Gravimetric Analysis (TGA)
TGA experiments were performed using a TA Q5000 IR instrument. SLMs (5-10 mg) were run at 5° C. min$^{-1}$ under $N_2$ purging at 50 mL min$^{-1}$ in platinum pans.
Dynamic Scanning Calorimetry (DSC)
DSC measurements were done using a TA Q200 instrument. Measurements were run under $N_2$ purging at 40 mL min$^{-1}$ and at 2° C. min$^{-1}$ with ~5 mg of SLM. Each measurement was performed in aluminum pans in the range of −10 to 100° C. with successive heat-cool cycles.

UV-Vis Absorption Spectroscopy

UV-Vis spectra were recorded on a Cary 5000 UV-Vis-NIR spectrophotometer (Agilent Technologies) in the range of 400 to 800 nm to obtain their percentage transparency.

X-Ray Diffraction (XRD):

XRD experiments on SLMs were performed using a Bruker D2 Phaser equipped with a beam of $\lambda_{CuK\alpha}$=0.15418 nm. The diffraction intensity of SLMs were recorded for 20 in the range of 4° to 80°.

Nanoindentation

Nanoindentation studies were performed on the samples using the Agilent Technologies G200 Nanoindenter. The machine continuously monitors the load, P, and the depth of the penetration, h, of the indenter with the resolutions of 1 nN and 0.2 nm, respectively. A Berkovich diamond tip indenter with the tip radius of ~100 nm is used for the indentation. A peak load, $P_{max}$ of 1 mN with the loading and unloading rates of 0.2 mN s$^{-1}$, Poisson's ratio of 0.3 and a hold time (at $P_{max}$) of 10 s was employed. A minimum of 125 indentations are performed in each case. The P-h curves were analyzed using the Oliver-Pharr method to extract the Young's modulus (E), and the hardness (H) of the samples. The yield strength, $\sigma_y$ was estimated using the relation $\sigma_y$=H/3.

Field Emission Scanning Electron Microscope (FESEM)

FESEM samples were prepared by sputtering a 10-20 nm layer of Pt/Pd/Au. Images were acquired using a Zeiss Ultra55/Supra55VP FESEM equipped with a field emission gun operating at 5-10 kV.

Solvent Resistance of SLMs

EC-SLMs (~10 mg) were fully immersed in 2 ml of hexane, chloroform, ethyl acetate, acetonitrile, absolute ethanol, methanol, dimethylformamide (DMF) or milli-Q water. After 24 h incubation, the SLMs immersed in solvents were removed and air-dried overnight to remove any traces of solvent. The weight of EC-SLMs before and after the incubation was noted. As EC-SLM disperses in water, its weight could not be obtained after the incubation.

Self-Regeneration of SLMs 5-10 mg of EC-SLM (first generation, Gen I) was added to 500 ml of lysogeny broth supplemented with carbenicillin incubated at 37° C. for 24 h. The cells were pelletized, casted on to the mold and air-dried to obtain the second generation, Gen II of EC-SLM (same fabrication protocol as described above). Similarly, a 5-10 mg fragment of Gen II was utilized to obtain the third generation, Gen III of EC-SLM.

Example 2: Evolution and Fabrication of SLMs

Figure 3A:
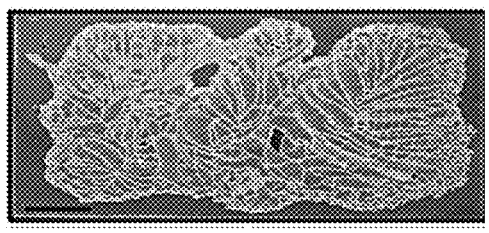
FIGS. 3(A)-3(W) present optical images illustrating the evolution of stiff living material (SLM). (A-I) *E. coli* pellet dried on glass substrate. (C, E-G) Pellet casted within a mold. (D-I) Higher pellet amount. (G) Arrows indicate ineffective drying of cells that inhibits formation of a cohesive glossy material. (H, I) Under low vacuum suction. (J, K) *E. coli* pellet dried on copper mesh substrate. *E. coli* pellet dried on (L) Stainless-steel mesh and (M) Polytetrafluoroethylene (PTFE) coated steel mesh substrates. (N) *E. coli* pellet dried on copper mesh at 50° C. for 24 h. (O-W) *E. coli* pellet dried on polyvinylidene fluoride (PVDF). Pellet dried at (O) 50° C. for 24 h, (P) 75° C. for 2 h, (Q) 75° C. for 3 h, (R) 75° C. for 6 h, (S) 100° C. for 1 h and (T) 100° C. for 2 h. (U, V) Low vacuum suction using Millipore SNAP i.d. Mini Blot Holder. (W) Pellet dried at ambient conditions (25° C., 24 h, 40±5% humidity). (A-F, H-J, L-W) Top surface. (G, K) Bottom surface.
Figure 3B:
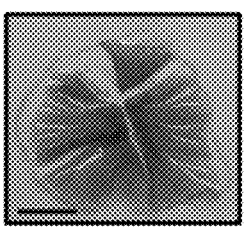
Figure 3C:
Figure 3D:
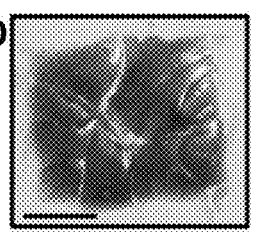
Figure 3E:
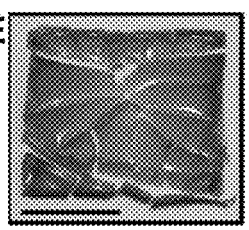
Figure 3F:
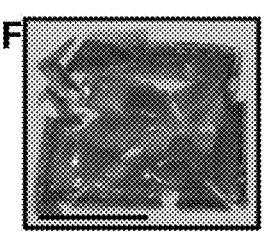
Figure 3G:
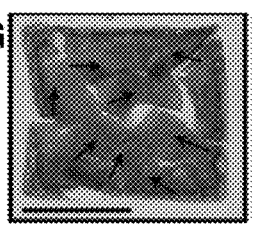
Figure 3H:
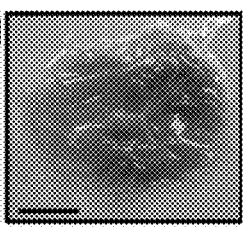
Figure 3I:
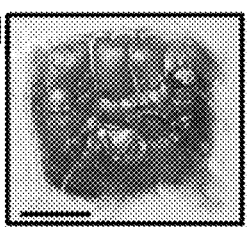
Figure 3J:
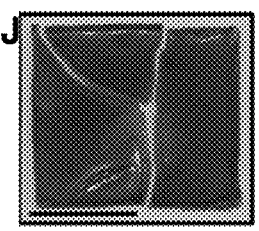

Engineered Living Materials (ELMs) may be defined as engineered materials composed of living cells that form or assemble the material itself, or modulate the functional performance of the material in some manner. All the ELMs reported so far are essentially soft materials in the form of biofilms, semi-solids or hydrogels that are produced by genetically engineering the extra-cellular matrix of living cells.(12-27) Notably, the stiff structural characteristic of the extra-cellular matrix (viz. curli fibers) can be exploited to fabricate a macroscopic stiff (2-4 GPa) plastic.(28) In contrast to these approaches, it was investigated whether the living cells (without the extra-cellular matrix) alone can be employed to produce a material, and in doing so, may be able to effectively incorporate life-like properties (e.g., self-regeneration, self-regulation, self-healing, environmental responsiveness and self-sustainability) into the resulting material. For this reason, the *Escherichia coli* strain PQN4 was cultured; the bacteria developed from LSR10 that has been shown to not produce extracellular components such as curli fibers, flagella or cellulose.(12) After culturing for 24 h in lysogeny broth media, *E. coli* was pelletized and washed with milli-Q water to remove the nutrient media. The so obtained pellet when drop-casted on a glass slide, upon ambient drying, resulted in a fragmented transparent living material that indicated its brittleness and the ability to form a cohesive material from cells (FIG. 3A). Increasing the amount of the pellet within a mold was found to slightly minimize the fragmentation of the living material. However, unlike the top surface (FIG. 3F), the bottom surface (FIG. 3G) of the living material was found to have patches of cells that were not dried effectively, inhibiting the formation of a cohesive glossy material. It was reasoned that the non-porous nature of the glass substrate might be contributing to ineffective drying of the bottom surface of the living material.

Figure 3K:
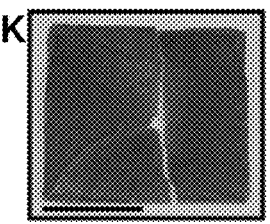
Figure 3L:
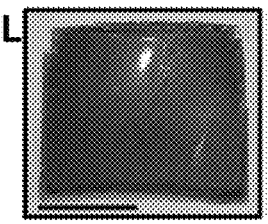
Figure 3M:
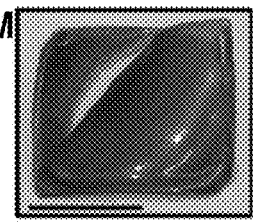
Figure 3N:
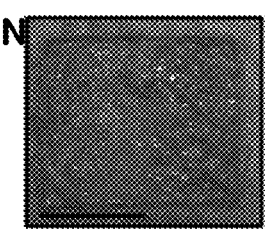
Figure 3O:
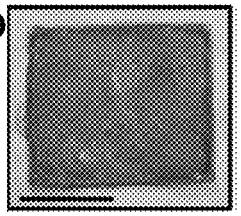
Figure 3P:
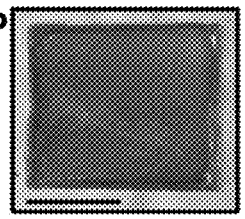
Figure 3Q:
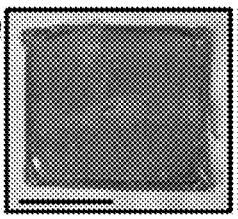
Figure 3R:
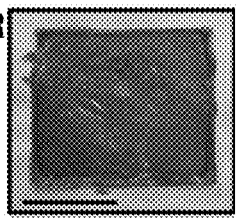
Figure 3S:
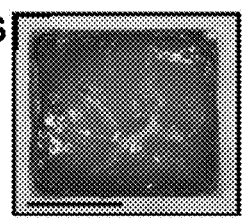
Figure 3T:
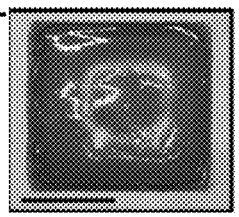
Figure 3U:
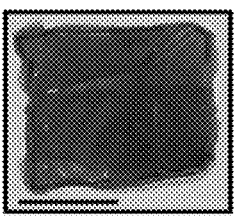
Figure 3V:
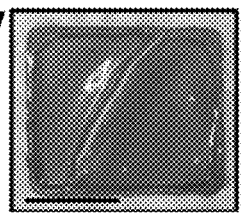
Figure 3W:
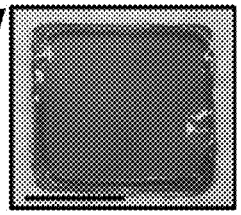
Figure 4:
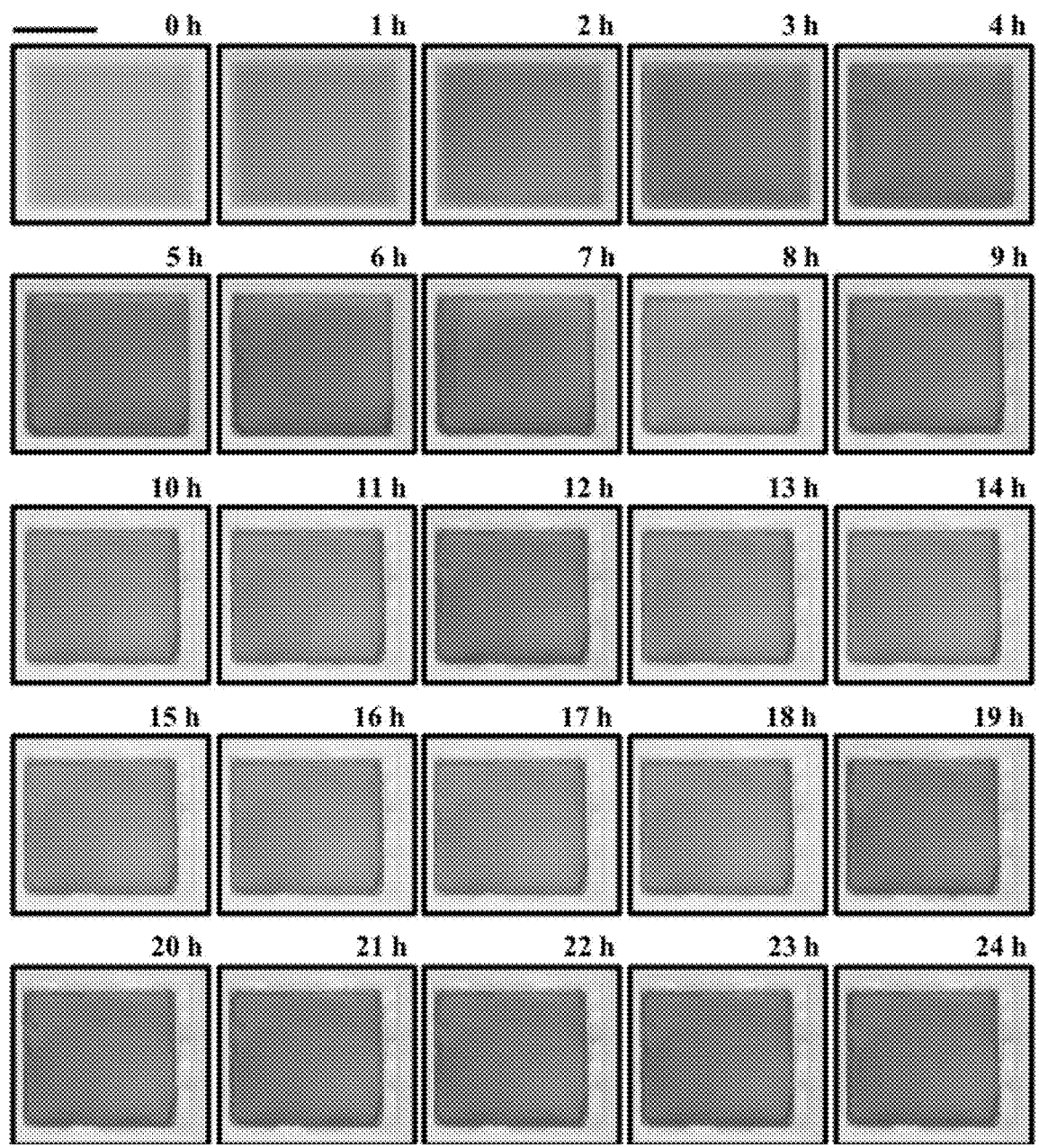
FIG. 4 presents optical time lapse images (recorded every hour) showing the ambient drying of EC-SLM. (Scale bar 1 cm.)
Figure 5:
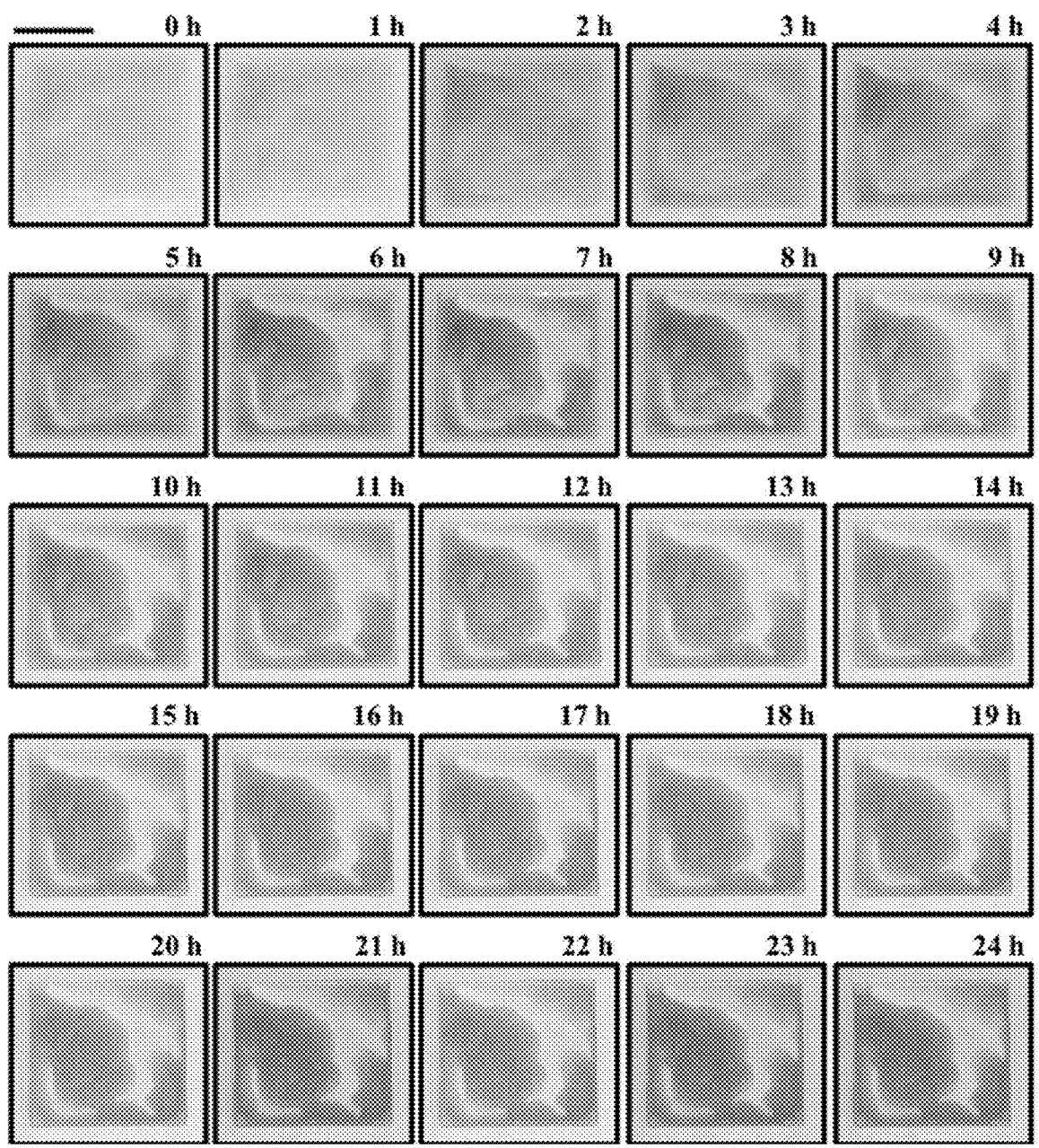
FIG. 5 presents optical time lapse images (recorded every hour) show the ambient drying of LR-SLM. (Scale bar 1 cm.)
Figure 6:
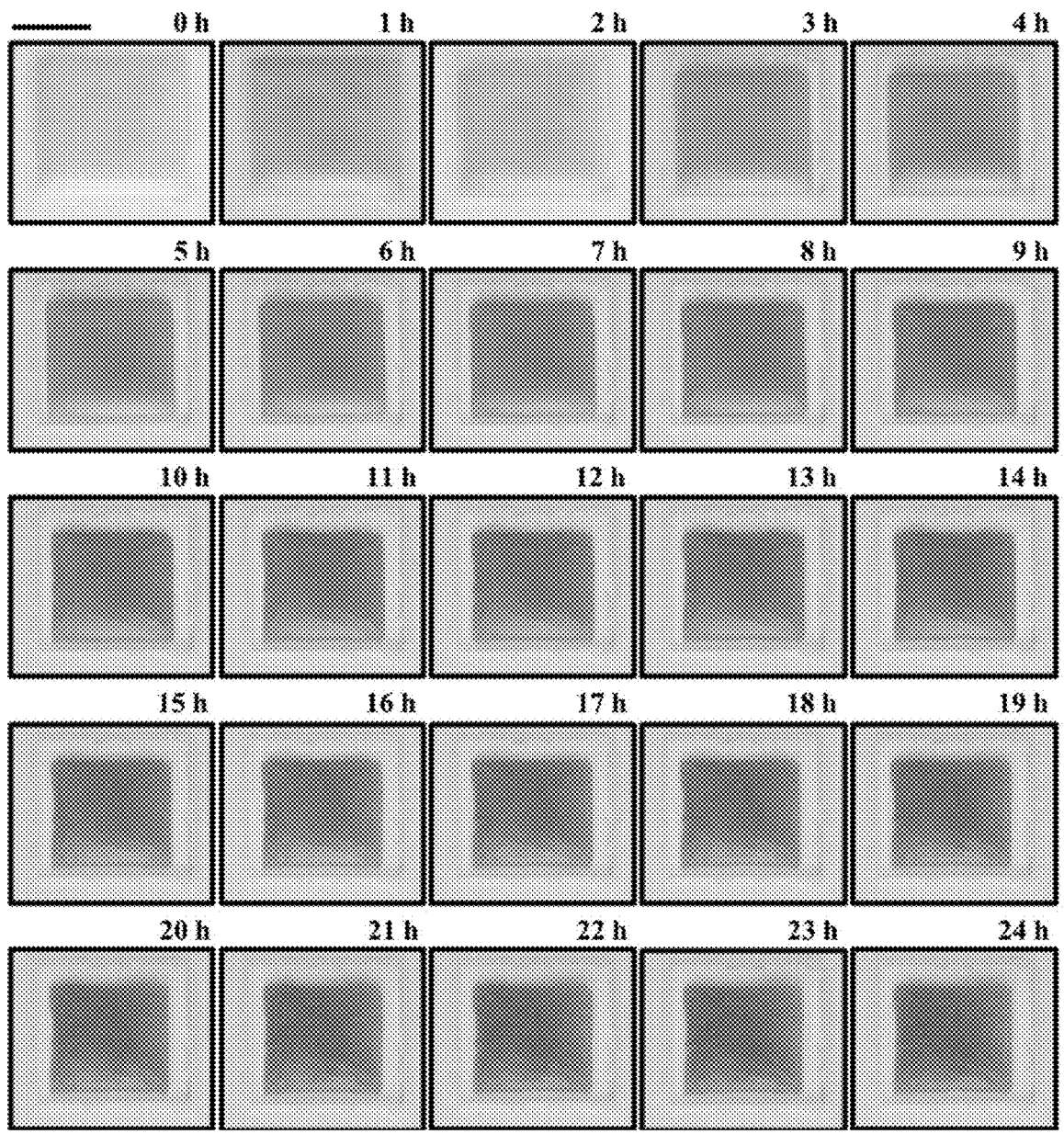
FIG. 6 Optical time lapse images (recorded every hour) show the ambient drying of SC-SLM. (Scale bar 1 cm.)
Figure 7A:
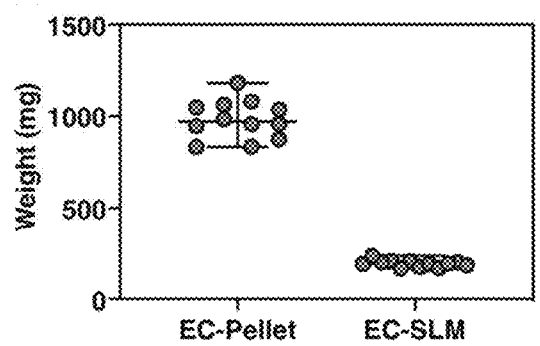
FIGS. 7(A)-7(D) depict weight analysis of SLM. (A) *E. coli* pellet weight before and after drying (24 h) to form the SLM. (B) *L. rhamnosus* pellet weight before and after drying (24 h) to form the SLM. (C) *S. cerevisiae* pellet weight before and after drying (24 h) to form the SLM. (D) Dry weight percentage of EC-SLM, LR-SLM and SC-SLM. The graphs show mean values and the error bars are standard deviation.
Figure 7B:
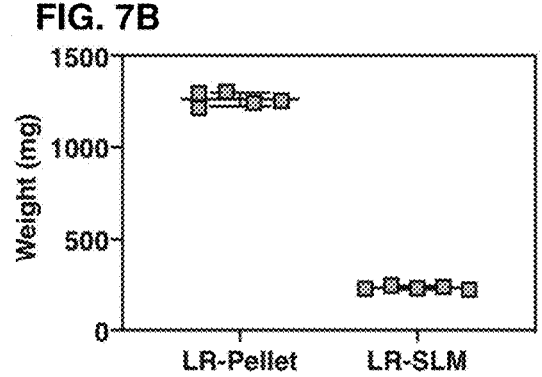
Figure 7C:
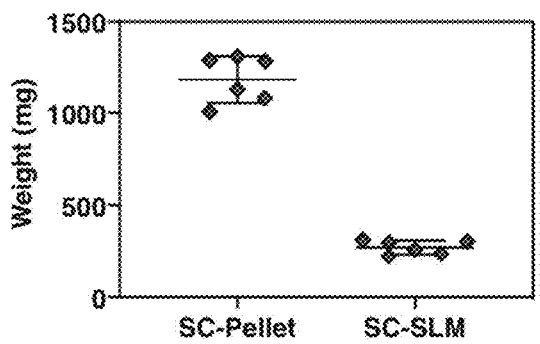
Figure 7D:
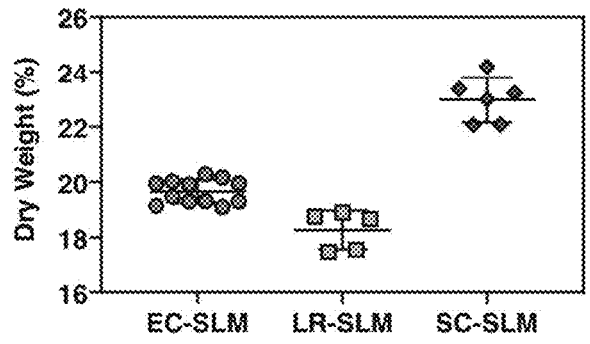

Drop casting on porous substrates like copper or stainless-steel mesh circumvented the cell patches but left imprint on the bottom surface of the living material (FIG. 3K). In case of nylon membrane, the living material was found to adhere to the substrate, which upon peeling off manually, left ineffectively dried cell patches all along the point of contact with the nylon matrix. On the hydrophobic surface of polytetrafluoroethylene (PTFE) coated stainless-steel, the living material deformed to a curved architecture. Although, the hydrophobic nature of the substrate prevents adhesion to living material, it was reasoned that adhesion to substrate and/or low vacuum suction might aid the fabrication of fragmentation-free and flat living material. Hydrophobic polyvinylidene fluoride (PVDF) membrane that is typically used in western blotting to bind proteins was employed as a substrate. By drop casting *E. coli* cell pellet on PVDF membrane mounted on a Millipore SNAP i.d. Mini Blot Holder, connected to a low vacuum suction, a flat living material was achieved, but with few fragments (FIGS. 3U, 3V). In the same latter set up, in the absence of low vacuum suction, fragmentation-free flat living materials were also fabricated by ambient drying on PVDF membranes. The strong adhesion of living material with the PVDF membrane did not facilitate its manual peeling but can be easily removed by gently wiping the membrane with dimethylformamide (DMF) solvent. Instead of ambient drying, use of higher temperature (50/75/100° C.) speeds up the formation of living materials but with extensive cracks and discoloration or charring (FIGS. 3N-3T).

TABLE 1

List of parameters and conditions employed during the fabrication of SLM.

| Parameter | Types/Conditions | Remarks |
| --- | --- | --- |
| Substrate | Glass | The bottom surface of SLM had scale-like architectures of patches of cells possibly due to ineffective drying on the non-porous nature of glass surface. SLM cracks extensively. |
| | Copper Mesh | The bottom surface of SLM lacked scale-like architectures. SLM cracks and it is non-flat. The mesh pattern gets imprinted on the bottom surface of SLM. |
| | Stainless Steel Mesh | The bottom surface of SLM lacked scale-like architectures. SLM cracks and it is non-flat. The mesh pattern gets imprinted on the bottom surface of SLM. |

TABLE 1-continued

List of parameters and conditions employed during the fabrication of SLM.

| Parameter | Types/ Conditions | Remarks |
|---|---|---|
| | Nylon Membrane | Adheres to nylon and the bottom surface of SLM had tiny scale-like architectures when peeled off from nylon. SLM Cracks. The mesh pattern gets imprinted on the bottom surface of SLM. |
| | Polytetra-fluoro-ethylene (PTFE) Coated Steel Mesh | SLM does not stick to PTFE. SLM Cracks and it is deformed to a non-flat (curvy) shape. |
| | Polyvinyl-idene fluoride (PVDF) | SLM adheres to PVDF that cannot be peeled off manually but can be removed by gently wiping with dimethyl-formamide (DMF) solvent. Flat and fragmentation-free SLMs can be obtained. |
| Temperature | 25/50/75/100 □ | Higher temperature speeds up the SLM formation but have disadvantages like extensive cracks, charring/discoloration (depending on temperature and duration) and enhanced cell death. At 25 □, the SLM formation takes up to 24 h. |
| Low Vacuum Suction | Millipore SNAP i.d. Mini Blot Holder Vacuum Desiccator | SLM formation speeds up when vacuum suction (unidirectional; from bottom side of the cell pellet) is applied via a blot holder. Blot holder set up can facilitate flat SLMs. The three-dimensional suction in a vacuum desiccator results in potholes on SLM that cracks and it is non-flat (highly curvy). Vacuum desiccator takes longer time for SLM formation. |
| Duration | 12/24/48 h (at 25 □) 1/2/3/6/24 h (at 50/75/100 □) | 24 h duration was found to be optimal for SLM formation at 25 □, while at 100 □, 1-3 h was sufficient but suffer from cracking, charring and/or higher cell deaths. |
| Lysing Cell | 70% Ethanol Treatment Ultra-sonication Freeze-Thawing | Ethanol treatment was found to be more convenient and effective than the other methods. |

Figure 1B:
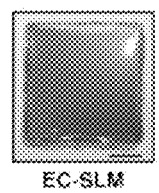
Figure 1C:
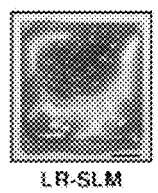
Figure 1D:
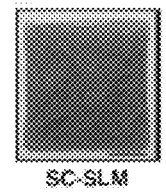
Figure 1E:
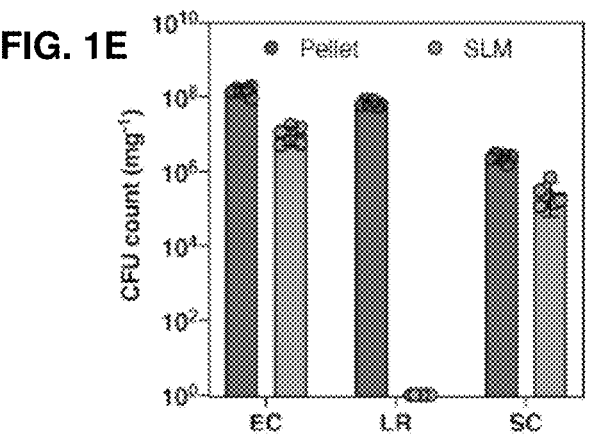
Figure 1F:
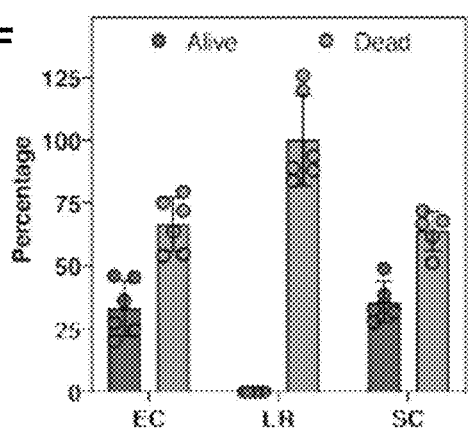
Figure 8:
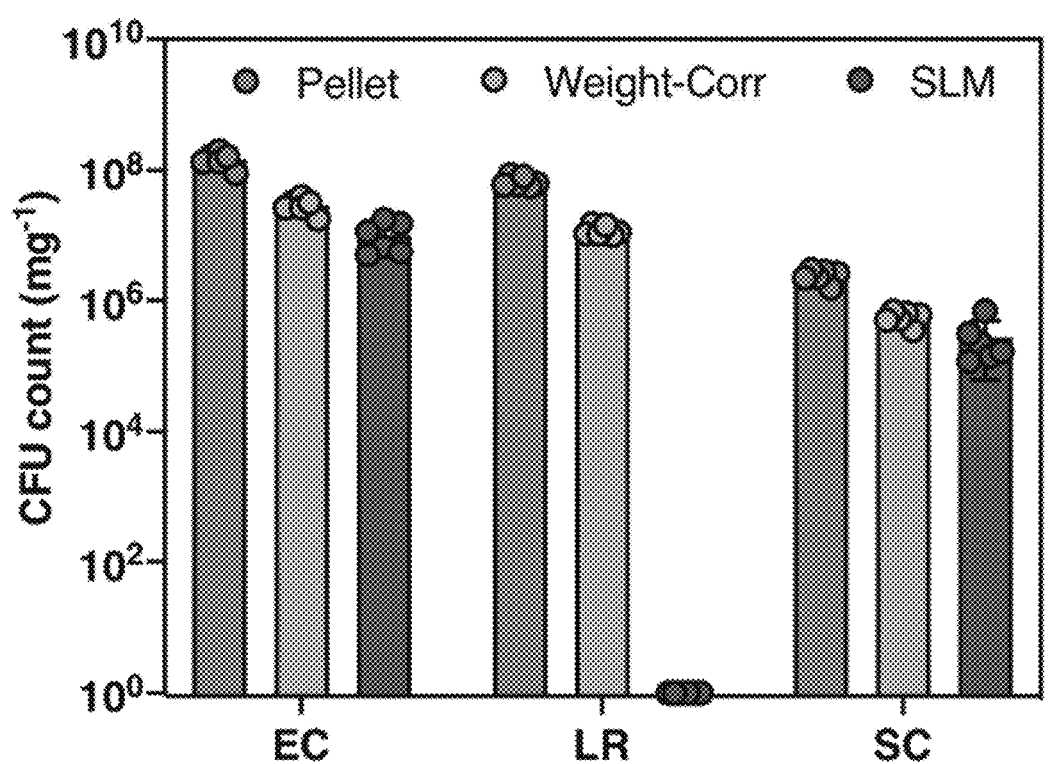
FIG. 8 depicts colony forming unit (CFU) analysis of SLM. CFU counts of *E. coli*, *L. rhamnosus* and *S. cerevisiae* of pellet, weight-con (pellet corrected for dry weight as per FIG. 7D) and SLM. The bar graphs represent mean values and the error bars are standard deviation.
Figure 9:
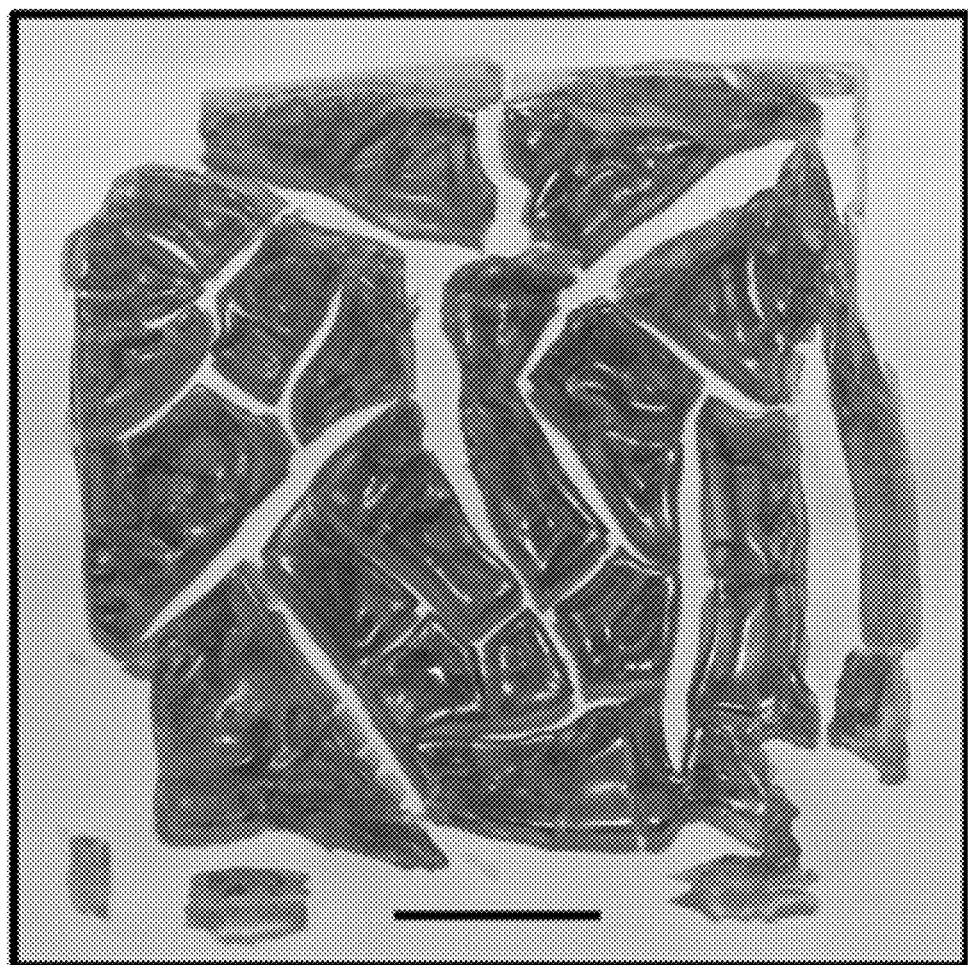
FIG. 9 depicts an optical image of SLM fabricated from 70% ethanol treated *E. coli* cells.

An optimized fabrication of the SLM involved firmly sandwiching the PVDF membrane between two polypropylene molds (FIG. 1A). Casting the *E. coli* cell pellet on top of PVDF membrane and drying at ambient conditions (25° C. and 40±5% relative humidity) for 24 h resulted in the fragmentation-free glossy flat SLM (FIG. 1B). Given that the SLM was fabricated from *E. coli* cells (denoted by EC-SLM), whether any of them were alive was investigated. Notably, one milligram of EC-SLM was found to have $1.0\pm0.5*10^7$ colony forming units (CFUs), while its precursor, the wet cell pellet had a CFU count of $1.5\pm0.04*10^8$ $mg^{-1}$ (FIG. 1E). The same protocols were employed for the Gram-positive *Lactobacillus rhamnosus* and the yeast *Saccharomyces cerevisiae* to investigate whether other microbes can also form SLMs similarly. Interestingly, *L. rhamnosus* resulted in a SLM (denoted by LR-SLM) with highly wrinkled top surface, while that from *S. cerevisiae* (denoted by SC-SLM) had extensive cracks and a non-glossy texture (FIGS. 1C, 1D). CFU analysis revealed that SC-SLM had $2.7\pm0.2*10^5$ $mg^{-1}$, but no cell was found to be alive in the LR-SLM (FIG. 1E). Further, in order to more accurately evaluate the relative abundances of live and dead cells in the EC-SLM, LR-SLM and SC-SLM, their weight was analyzed before and after the drying procedure (FIG. 7). From this analysis, it was estimated that the CFU counts for pellets of *E. coli, L. rhamnosus* and *S. cerevisiae* that were corrected for their dry weights (FIG. 8). It was notable to find that 35.1%, 0% and 50.3% of the cells were alive in EC-SLM, LR-SLM and SC-SLM, respectively (FIG. 1F). However, the SLM fabricated from lysed *E. coli* cells treated with 70% ethanol were found to fragment extensively and the CFU analysis expectedly did not show any living cells in the SLM (FIG. 9). Thus, the very first examples of living bulk materials fabricated entirely from viable microbial cells were demonstrated.

Example 3: Physical Characteristics of SLMs

Figure 10A:
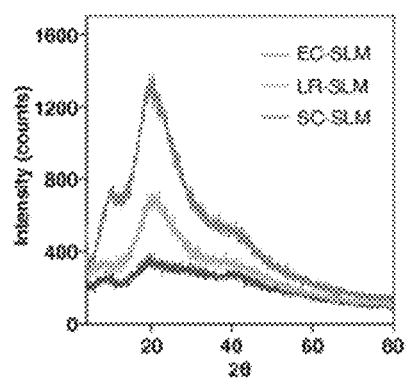
FIGS. 10(A)-10(I) depict the physical and structural characteristics of SLMs. (A) X-ray diffraction shows amorphous nature of SLMs. (B) Young's modulus and (C) Hardness of SLMs obtained from nanoindentation (n≥125). The graphs show median and the range. Field emission scanning electron microscopy (FESEM) images of (D, E) EC-SLM; (F, G) LR-SLM and (H, I) SC-SLM. (D, F, H) Top surface of SLM. (E, G, I) Cross-section of SLM. (Scale bar 2 μm.) (E, H) show the planar packing density, h (number of neighboring cells within the same plane).
Figure 12A:
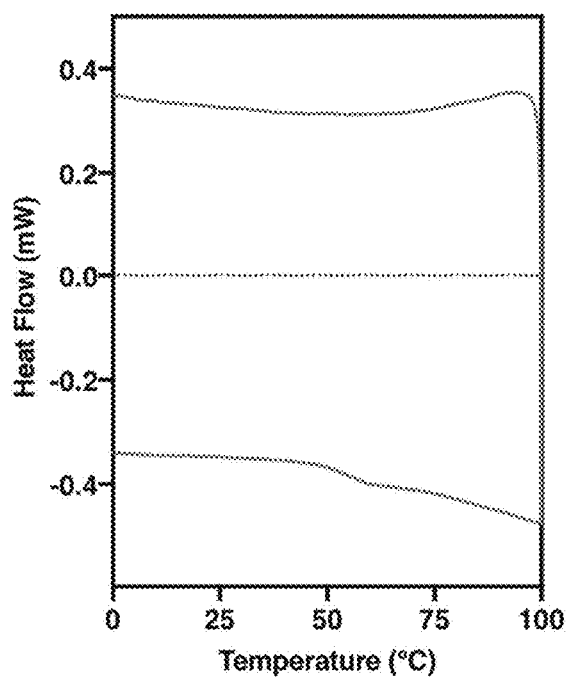
FIGS. 12(A)-12(C) present the differential scanning calorimetry (DSC) analysis of EC-SLM. DSC curve showing heating and cooling profiles of EC-SLM (A) first cycle, (B) second cycle and (C) third cycle.
Figure 12B:
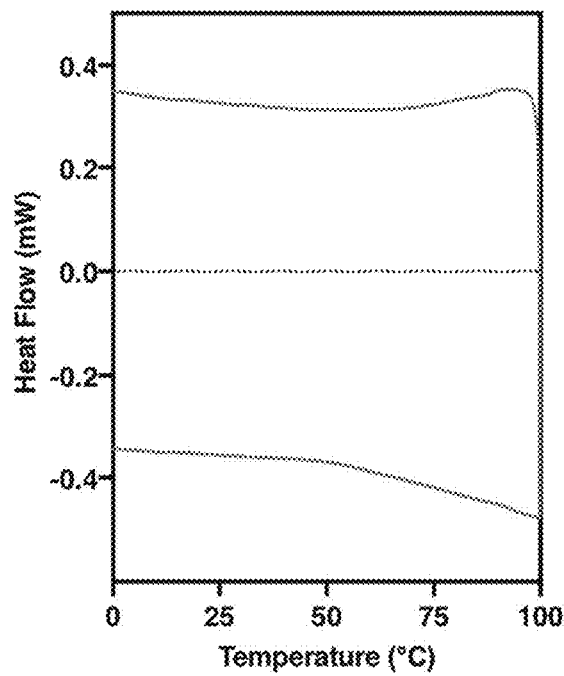
Figure 12C:
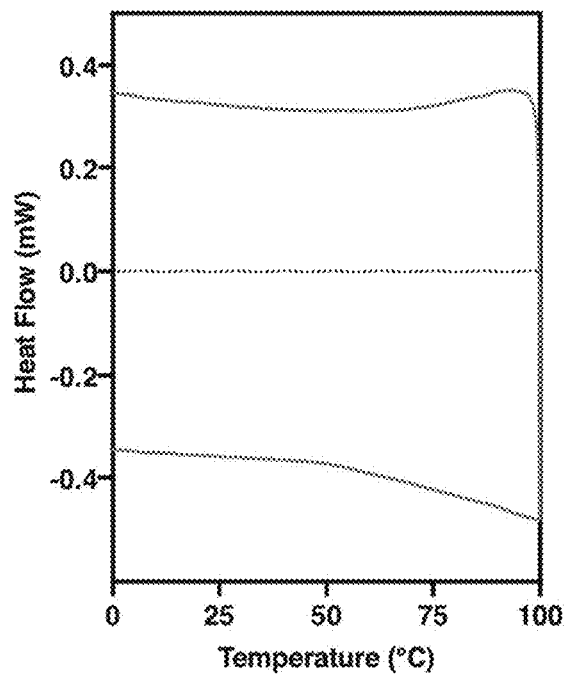
Figure 13A:
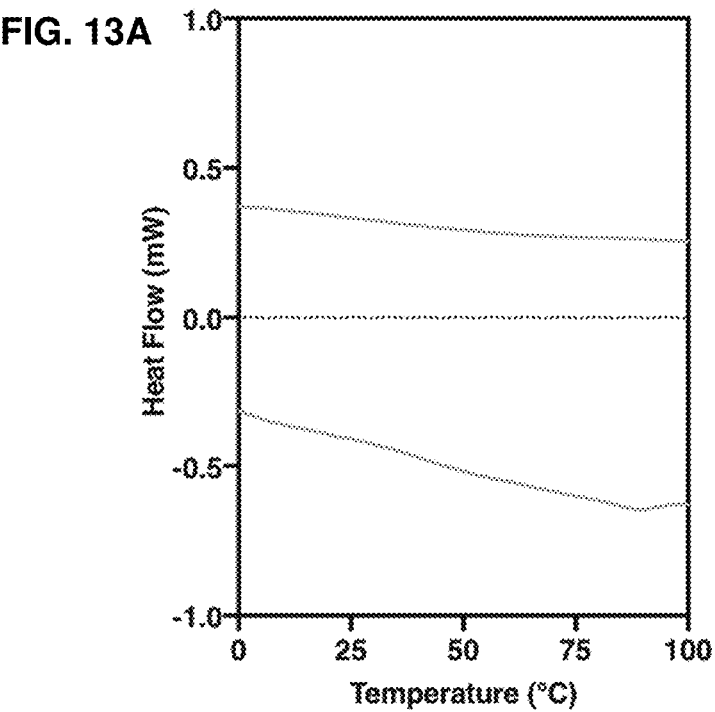
FIGS. 13(A) and 13(B) show the differential scanning calorimetry (DSC) analysis of SLM. DSC curve showing heating and cooling profiles of (A) LR-SLM and (B) SC-SLM.
Figure 13B:
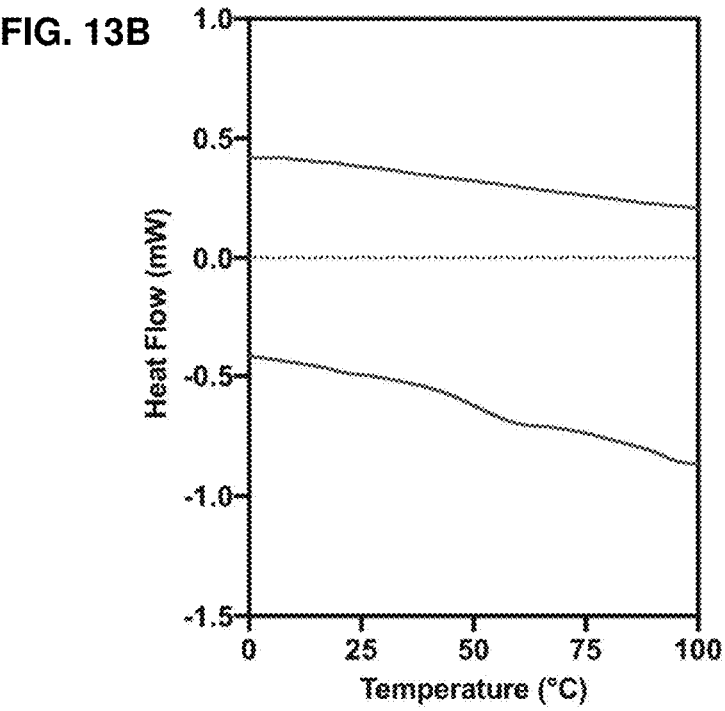
Figure 14A:
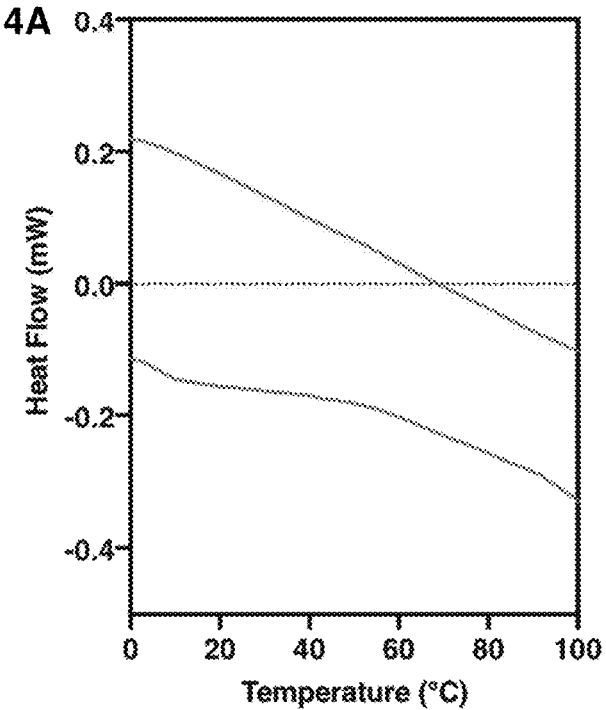
FIGS. 14(A) and 14(B) show the differential scanning calorimetry (DSC) analysis of SLM obtained from 70% ethanol treated *E. coli*. DSC curve showing heating and cooling profiles of (A) first cycle and (B) second cycle.
Figure 14B:
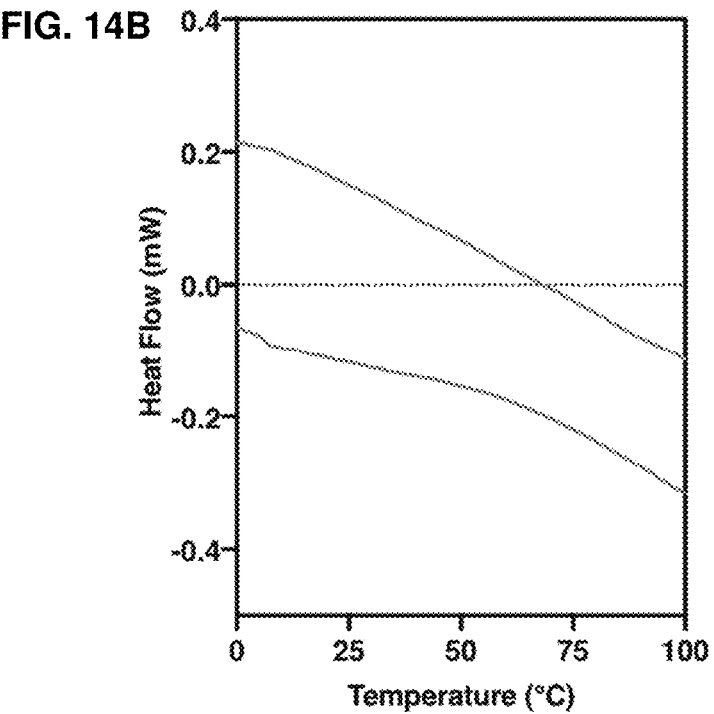
Figure 15A:
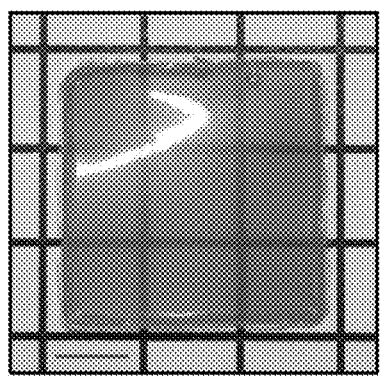
FIGS. 15(A)-15(C) depict optical transparency studies of SLMs. Optical images show the transparency of (A) EC-SLM, (B) LR-SLM and (C) SC-SLM.
Figure 15B:
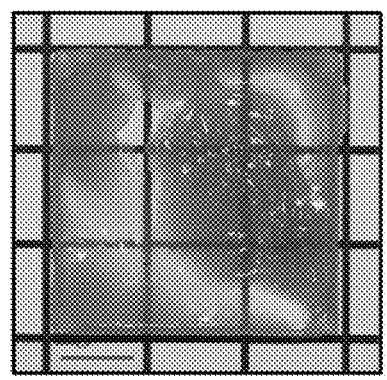
Figure 15C:
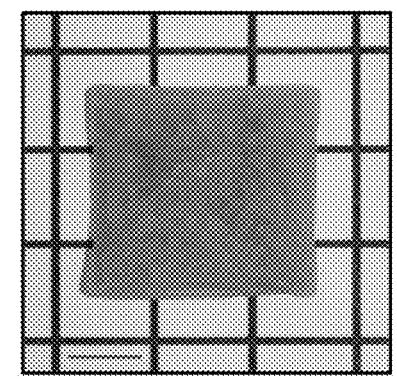
Figure 15D:
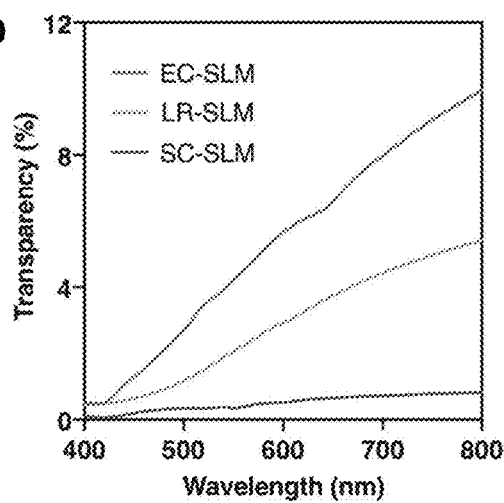
FIG. 15(D) depicts the absorption spectrum showing the percentage transparency of EC-SLM, LR-SLM and SC-SLM in the visible range.
Figure 16A:
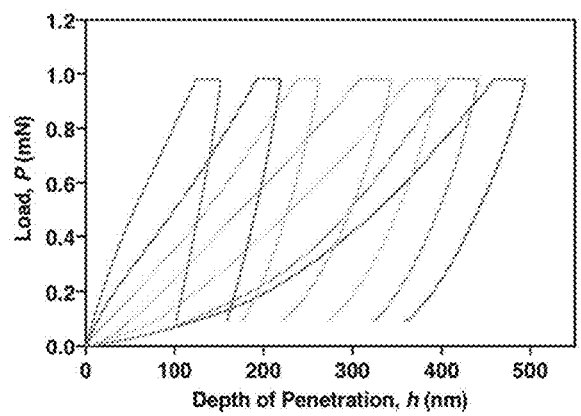
FIGS. 16(A)-16(D) show nanoindentation studies of SLMs. Representative load, P, verses depth of penetration, h, plots of (A) EC-SLM, (B) LR-SLM, (C) SC-SLM and (D) SLM obtained from 70% ethanol treated *E. coli*.
Figure 16B:
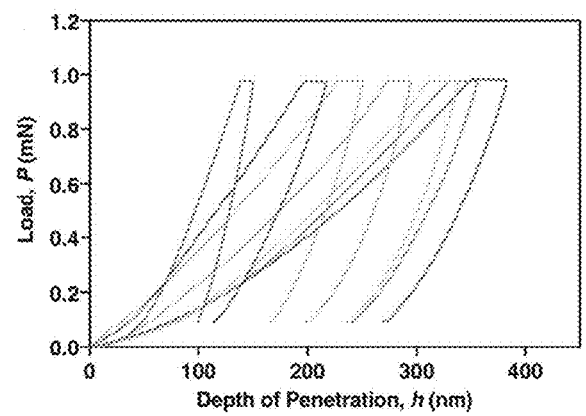
Figure 16C:
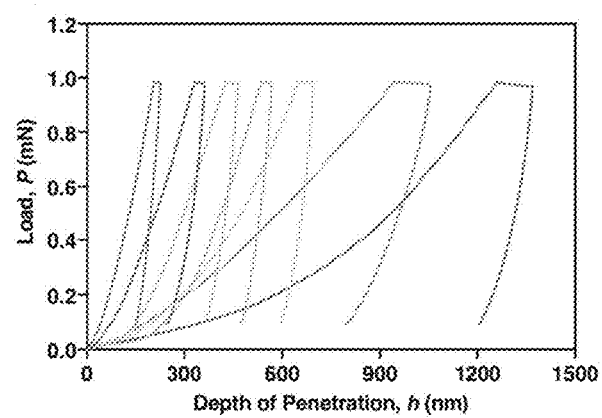
Figure 16D:
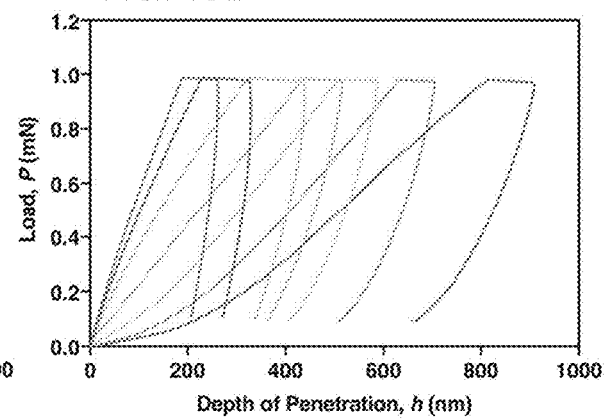

SLMs were first subjected to X-ray diffraction (XRD) to decipher any order arising due to self-assembly of cellular components. XRD spectra shown in FIG. 10A indicate that both EC-SLM and LR-SLM have a main diffraction peak corresponding to a d-spacing value of 0.44 nm, while EC-SLM has two additional ordering of 0.88 nm and 0.23 nm (FIG. 10A). Although, it is difficult to assign the identity of these peaks, XRD spectra do establish that SLMs are amorphous materials. Thermal gravimetric analysis (TGA) of SLMs showed that the material degrades above 130° C., while the earlier weight loss could be attributed to loss of water (FIG. 11). Differential scanning calorimetry (DSC) investigation of EC-SLM showed a glass-transition-like second-order transition (50-60° C.) during the first cycle of the heating curve (FIG. 12). However, the successive second and third cycles of DSC did not reveal the presence of such transitions, which can be attributed to the probable role of water acting as a plasticizer. Similar features were also observed for the DSC traces of LR-SLM and SC-SLM (FIG. 13). EC-SLM appeared to be transparent but the absorption spectra recorded in the visible range clearly showed that SLMs have less than 10% transparency (FIG. 15).

Example 4: Mechanical Characteristics of SLMs

Figure 10B:
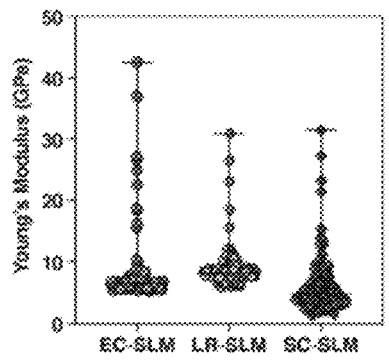
Figure 10C:
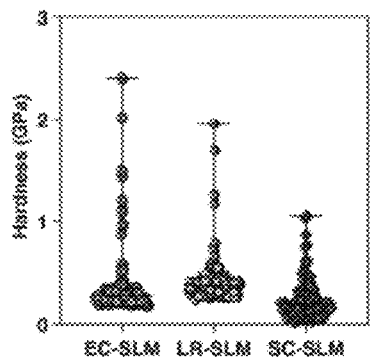
Figure 17A:
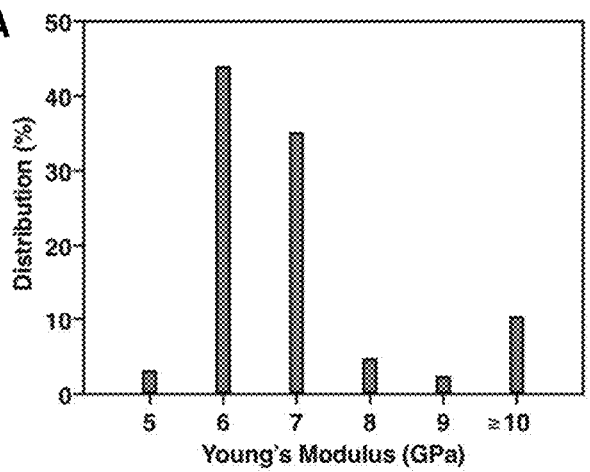
FIGS. 17(A)-17(C) show distribution of Young's modulus of SLMs. Percentage distribution of Young's modulus (data shown in FIG. 10B) obtained by nanoindentation on (A) EC-SLM, (B) LR-SLM and (C) SC-SLM. Herein, the Young's modulus value was counted as "n" for any values within n±0.5, while that above 10 GPa were also included with 10±0.5.
Figure 17B:
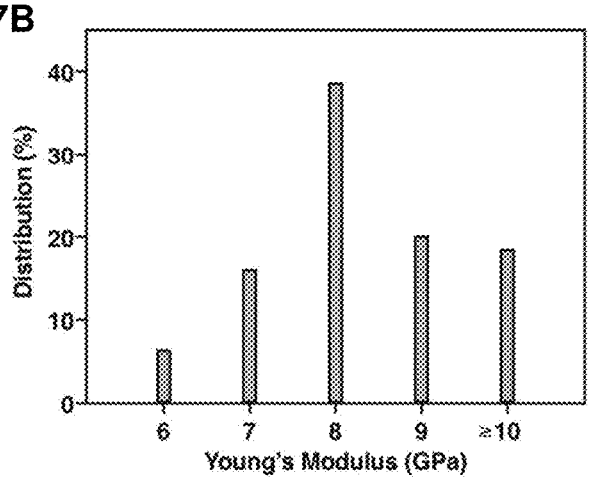
Figure 17C:
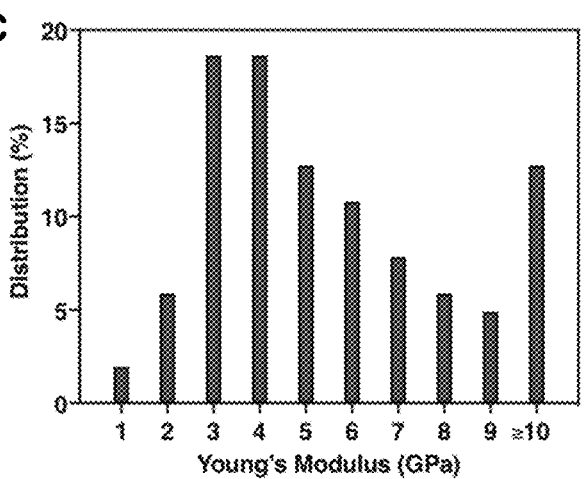
Figure 18A:
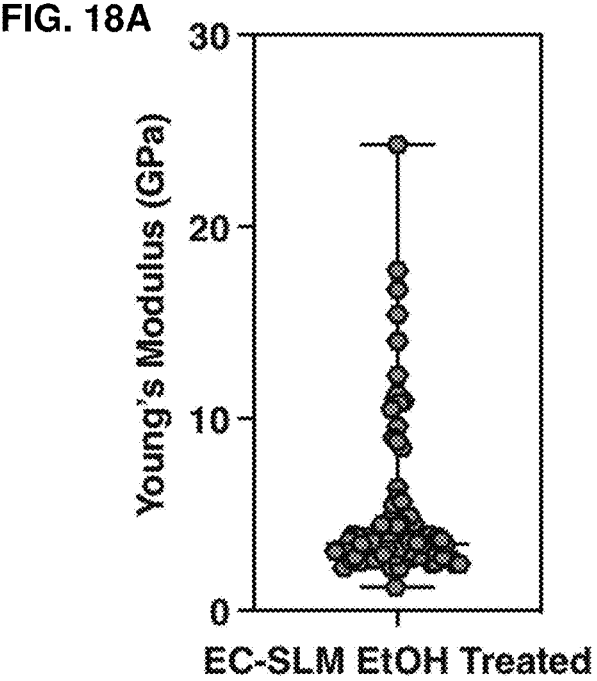
Figure 18B:
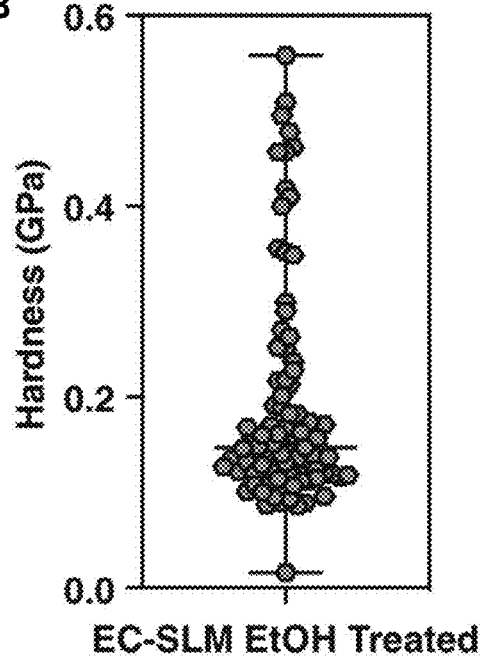
Figure 19:
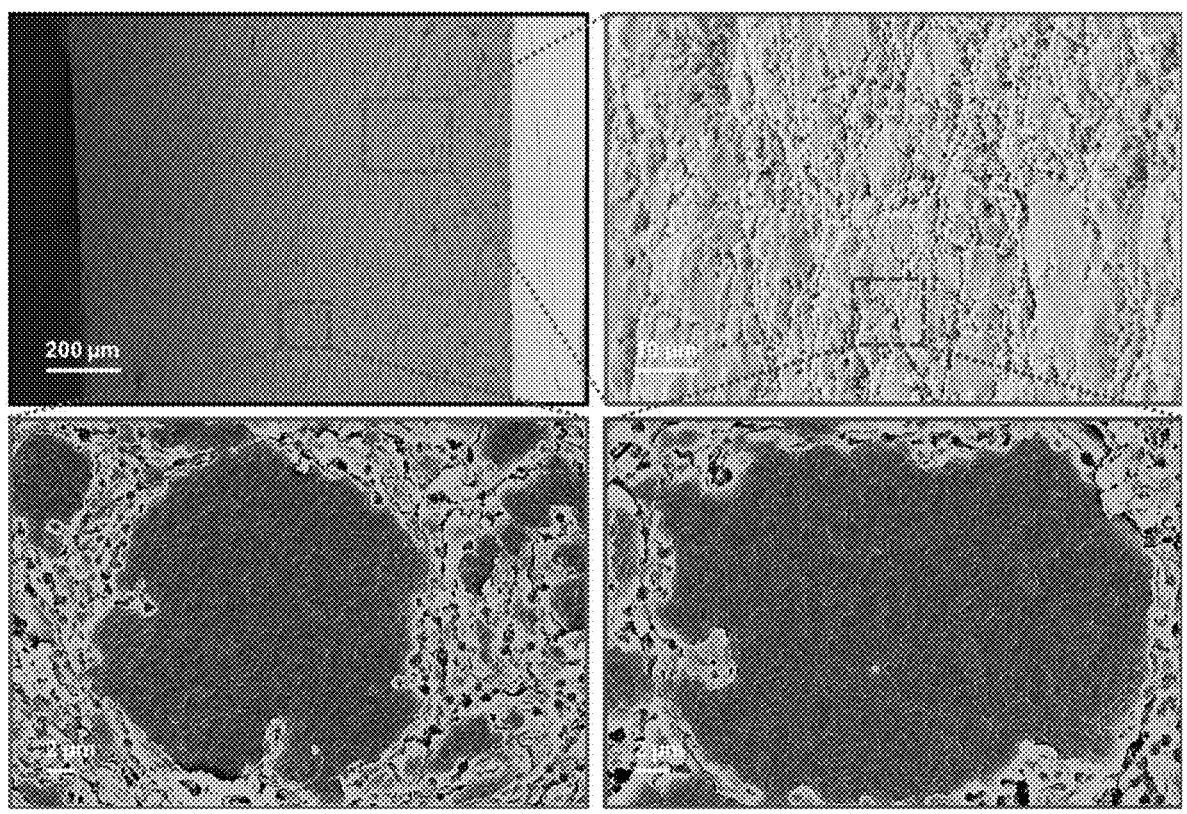
FIG. 19 shows field emission scanning electron microscopy (FESEM) images depicting the cross-sectional view of EC-SLM.
Figure 20:
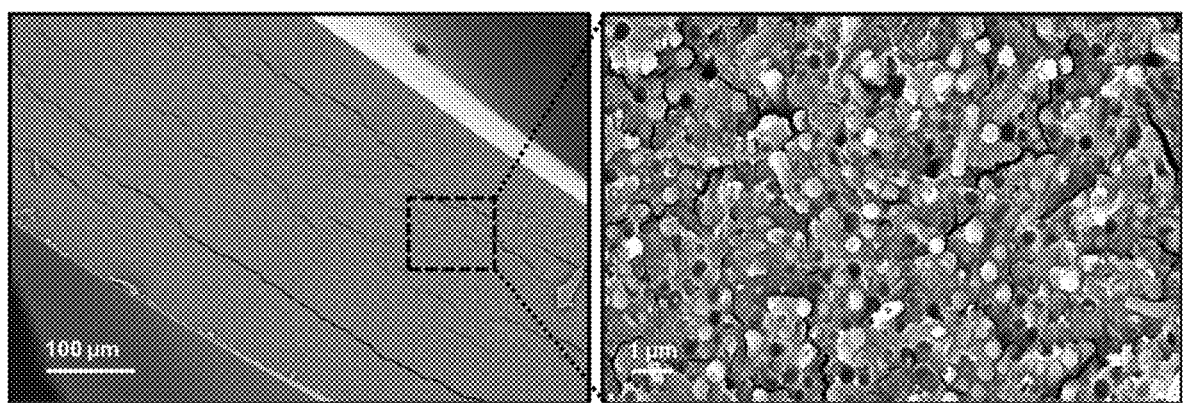
FIG. 20 shows field emission scanning electron microscopy (FESEM) images depicting the cross-sectional view of LR-SLM.

The mechanical properties of the SLMs were investigated by using the nanoindentation technique, as it offers small loads that are suitable for molecular materials and enables probing of microscopic dimensions as well as heterogeneity. (29, 30) SLMs were indented (n≥125) with a Berkovich diamond tip to obtain the continuous load, P, verses depth of penetration, h, curves. Nanoindentation experiments showed smooth P-h curves, which were analyzed using the Oliver-Pharr method to extract Young's modulus, E, and hardness, H, of the SLMs (FIG. 16). EC-SLM was found to have E ranging from 5 to 42 GPa, while their H were about 0.2 to 2.4 GPa (FIGS. 10B, 10C). LR-SLM (E=6-31 GPa, H=0.2-2 GPa) and SC-SLM (E=1-32 GPa, H=0.02-1 GPa) also showed stiffness and hardness in the similar range of EC-SLM (FIGS. 10B, 10C). However, a careful examination revealed that nearly 44% of the E values of EC-SLM were 6±0.5 GPa and 35% were 7±0.5 GPa. On the other hand, LR-SLM had a broader distribution of E values with about 39% of 8±0.5 GPa, while SC-SLM had an even broader distribution. This stiffness distribution of SLMs was consistently observed across different samples, which could be attributed to the packing of heterogenous components (FIG. 17). Interestingly, the SLM obtained from lysed *E. coli* (70% ethanol treatment) also exhibited similar E and H values, which further supports that cellular components can self-assemble, albeit heterogeneously, to form stiff materials (FIG. 18).

Example 5: Structural and Morphological Characteristics of SLMs

Figure 10D:
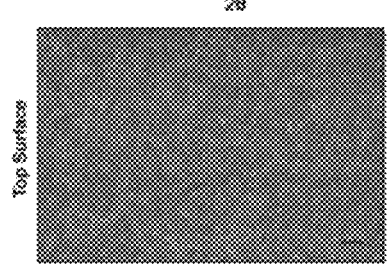
Figure 10F:
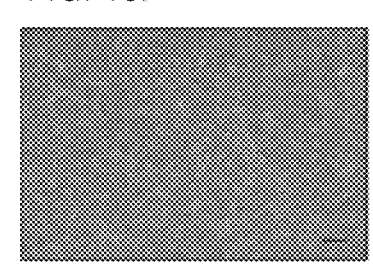
Figure 10H:
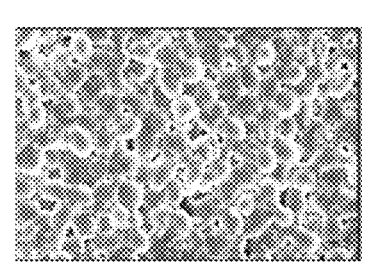
Figure 10E:
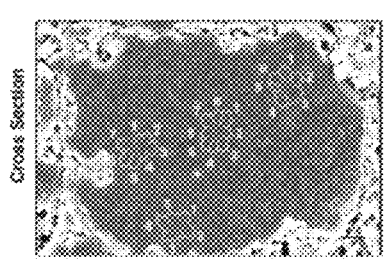
Figure 10G:
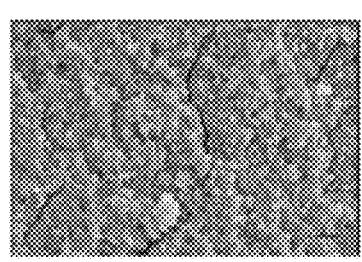
Figure 10I:
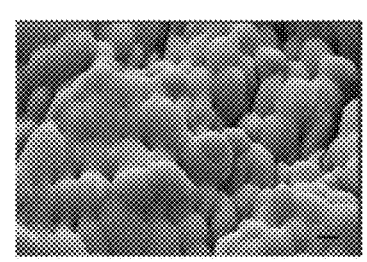
Figure 11A:
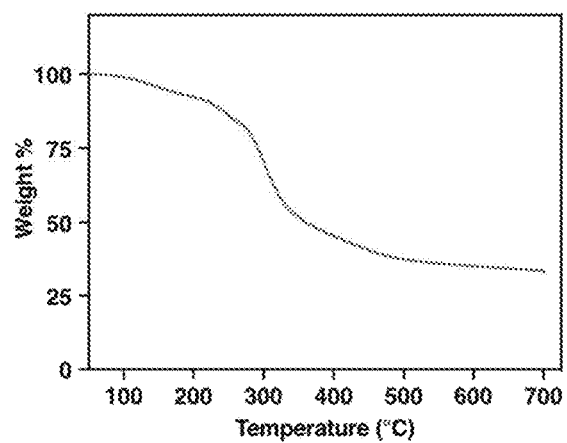
FIGS. 11(A)-11(D) present the thermal gravimetric analysis (TGA) of SLMs. TGA of (A) EC-SLM, (B) LR-SLM, (C) SC-SLM and (D) SLM obtained from 70% ethanol treated *E. coli* cells.
Figure 11B:
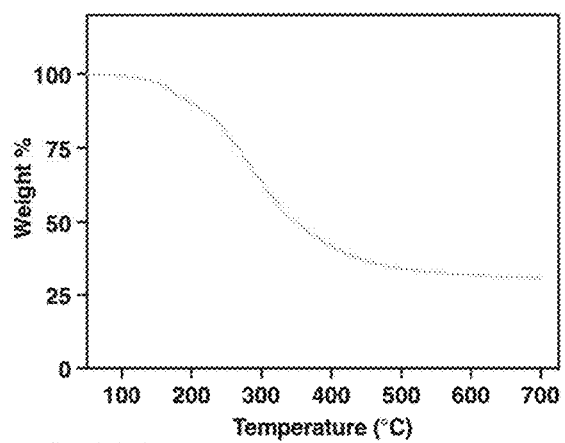
Figure 11C:
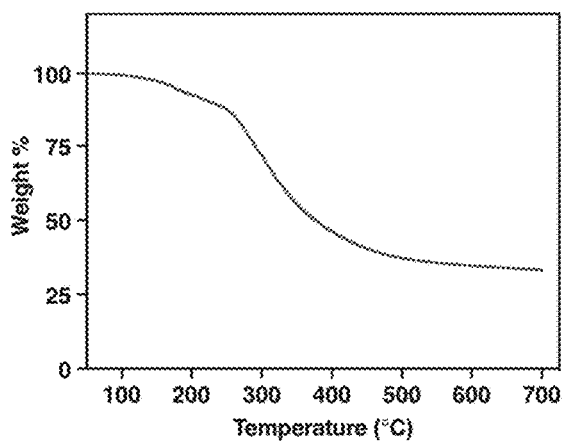
Figure 11D:
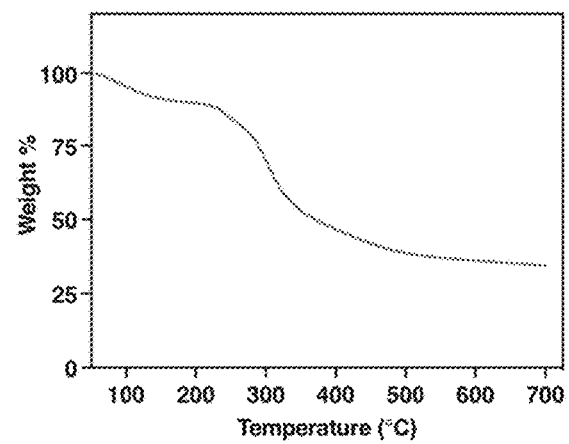
Figure 21:
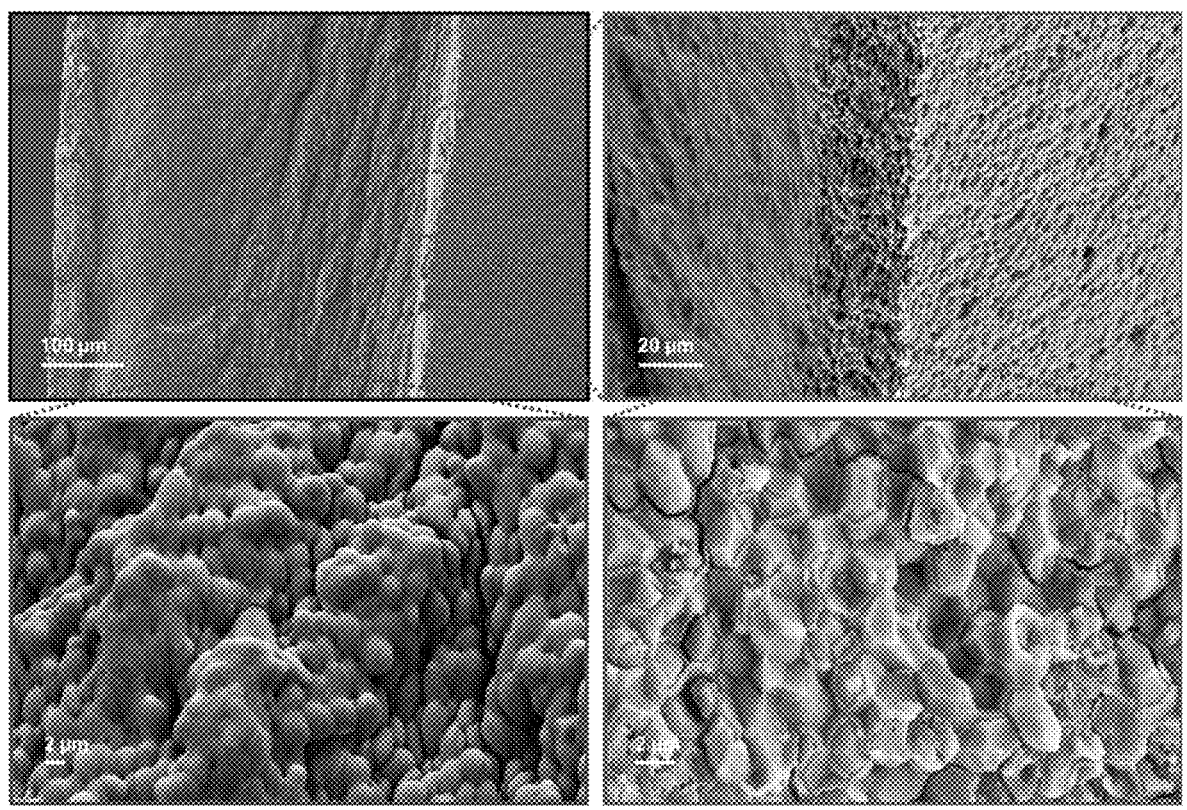
FIG. 21 shows field emission scanning electron microscopy (FESEM) images depicting the cross-sectional view of SC-SLM. The outer layers (both the top and bottom) of the SLM were tightly packed, while the core was relatively less tightly packed.

As SLMs are formed exclusively from microbial cells, their organization in the material that not only enables them to be alive but also stiff was investigated. Field emission scanning electron microscopy (FESEM) imaging of the top surface of EC-SLM revealed closely packed *E. coli* cells that appear to be ruptured (FIG. 10D). But from CFU analysis, it was determined that *E. coli* cells are alive in EC-SLM, which prompted investigation of the core of the material. Cross-sectional imaging of EC-SLM showed ordering of cells into tightly packed domains amidst loosely bound cells (FIG. 10E). Each domain could comprise of anywhere between 3 to nearly 500 cells, spanning up to a width of 30 μm. Notably, *E. coli* is a rod-shaped cell but, in these domains, transforms to a polygonal prism with a planar packing density (η, number of surrounding cells within the same plane; as seen from the images) of predominantly 6. The cells in the loosely bound regions may have greater survivability compared to the tightly packed domains. On the other hand, the top surface of LR-SLM was found to have an array of *L. rhamnosus* cells, whose rod-shape structure appeared to be intact (FIG. 10F). Herein, it is difficult to ascertain the η of *L. rhamnosus* due to their known inherent tendency to form chains. Further, the cross-sectional images of LR-SLM revealed that the cells were lysed to form an amorphous heterogenous solid (FIG. 10G). These FESEM images of LR-SLM provide additional evidence for their CFU data of no living cells (FIGS. 1E, 1F). In contrast, SC-SLM was found to form a close packing of spherical shaped *S. cerevisiae* cells with η of 6, while 5 and 7 were also observed (FIG. 10H). Interestingly, the cross section of SC-SLM showed, *S. cerevisiae* cells were packed less densely at the core but formed tightly compressed layers both on the top and bottom surfaces (FIG. 10I, FIG. 21). Thus, it appears that lysis of *S. cerevisiae* cells forms a hard-protective shell on the outer surface and thereby enables cells at the core to survive to a greater extent.

Example 6: Self-Regeneration of SLMs

Figure 22A:
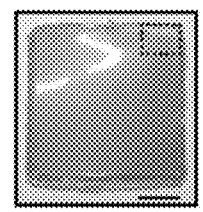
FIGS. 22(A)-22(E) depict the self-regeneration of EC-SLM. (A) Optical images of first (Gen I), second (Gen II) and third (Gen III) generations of EC-SLM. A small fragment (dotted rectangle) of Gen I was cultured, pelletized and air-dried to produce the Gen II, which in turn resulted in Gen III. (B) CFU count of Gen II and Gen III of EC-SLM. (C) Young's modulus and (D) Hardness of Gen II and Gen III of EC-SLM obtained from nanoindentation n≥125). (E) Time dependent CFU analysis of EC-SLM.
Figure 22A:
Figure 22A:
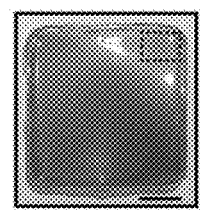
Figure 22A:
Figure 22A:
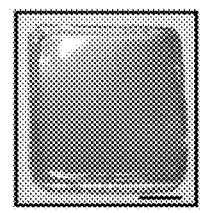
Figure 22B:
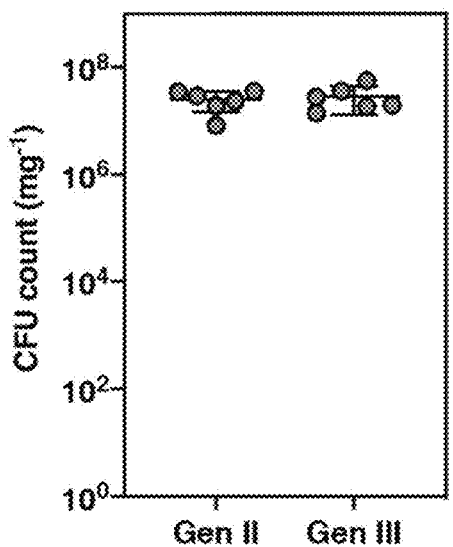
Figure 22C:
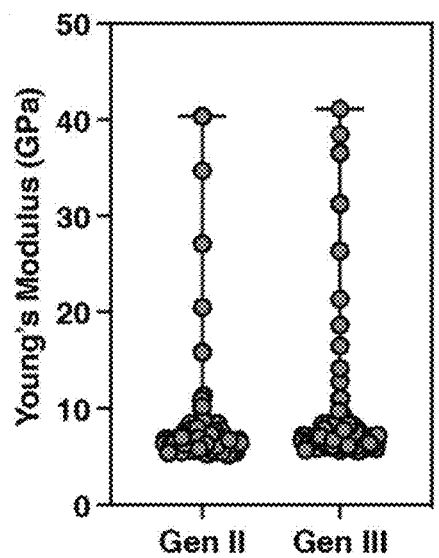
Figure 22D:
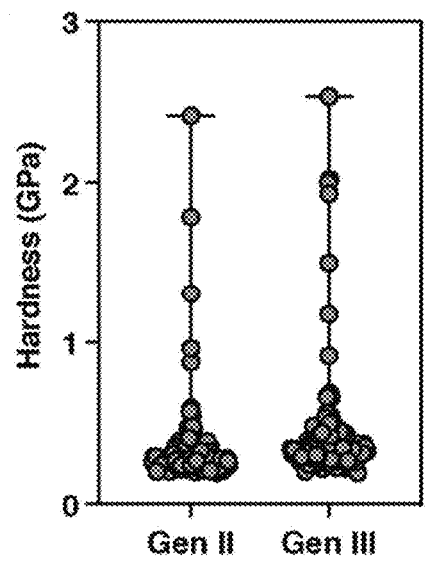
Figure 22E:
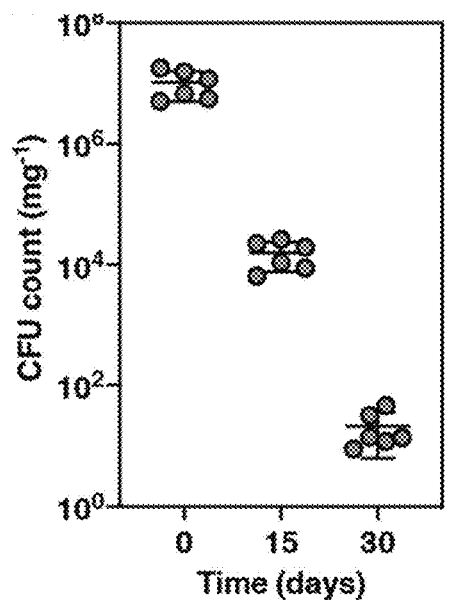

The living cells embedded in the SLMs were then exploited to develop a self-regenerating material. When a fragment of EC-SLM was introduced into selective lysogeny broth media, the SLM started to disperse and the cells self-replicated to form the turbid culture. After 24 h of culture, the cells were pelletized and casted onto the mold as per the same fabrication protocol described above. Ambient drying of the pellet for 24 h resulted in the second generation (denoted by Gen II) of EC-SLM fabricated from its first generation (denoted by Gen I, FIG. 22A). Similarly, a tiny fragment (5-10 mg) of Gen II was utilized to fabricate the third generation (denoted by Gen III) of EC-SLM. Both Gen II and Gen III were found to have a CFU count of around 107 mg-1, which is almost same as that of Gen I (FIG. 22B). Moreover, nanoindentation studies showed that E (5-41 GPa) and H (0.2-2.5 GPa) of self-regenerated EC-SLM (Gen II and Gen III) were also similar to that of the parent EC-SLM (FIGS. 22C, 22D). Further, in order to understand the survivability of the cells in the EC-SLM, time-dependent CFU analysis was performed (FIG. 22E). At day 15, the CFU count of EC-SLM was reduced to ~104 mg-1 and at day 30, it was about 21 mg-1. From this exponential decay data, the calculated cell death rate was found to be 0.43 per day.

Example 7: Robustness of SLMs

Figure 23:
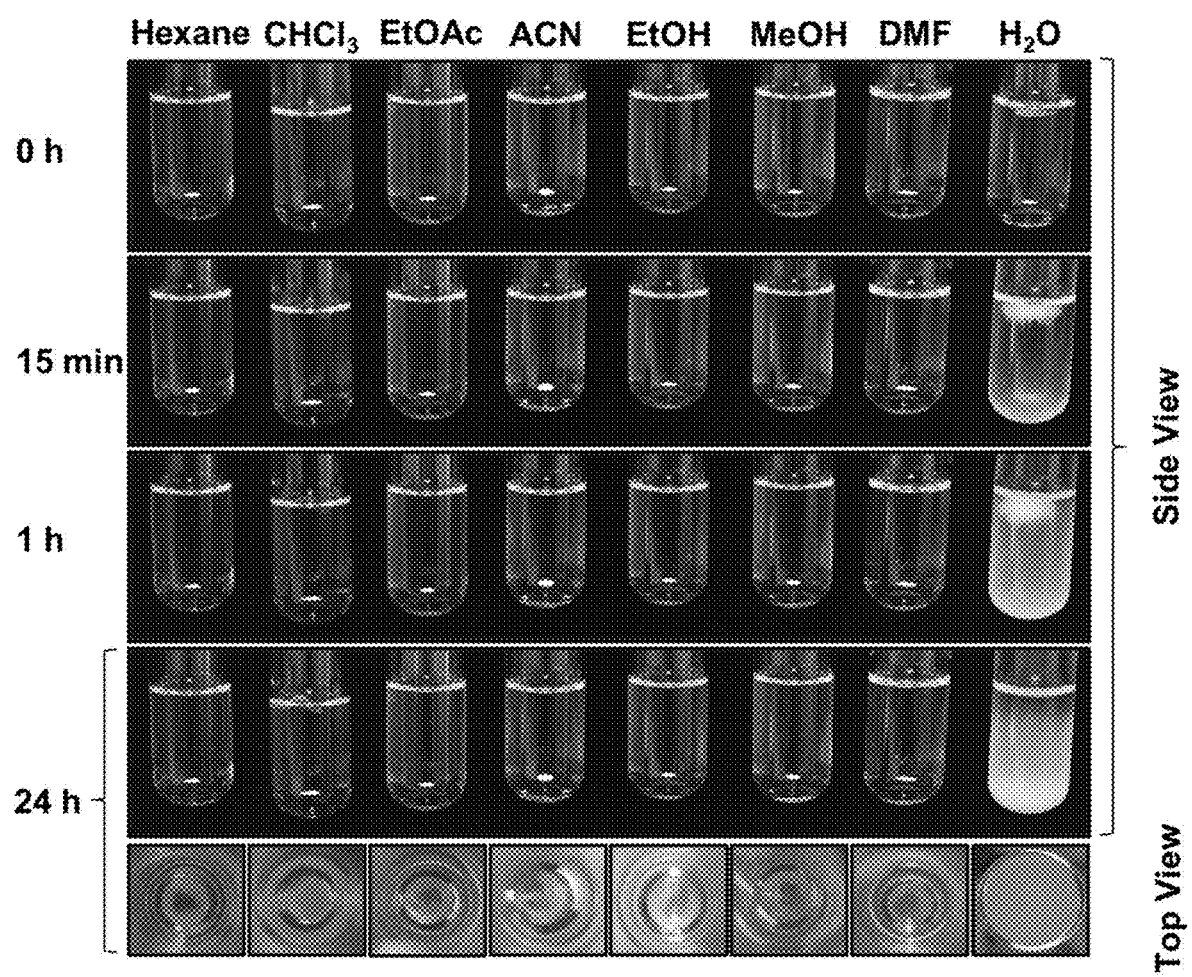
FIG. 23 depicts optical images of EC-SLM in various solvents over 24 h. $CHCl_3$: chloroform, EtOAc: ethyl acetate, ACN: acetonitrile, EtOH: absolute ethanol, MeOH: methanol, DMF: dimethylformamide.
Figure 24A:
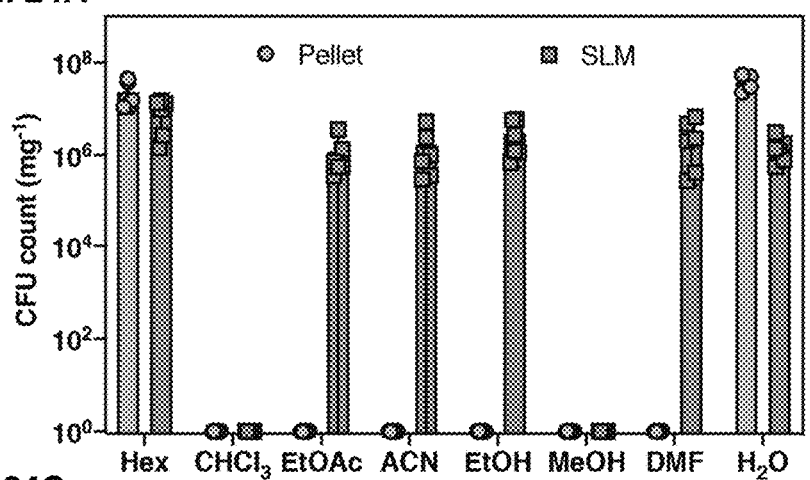
FIGS. 24(A)-24(C) show the robustness of EC-SLM. (A) CFU count of EC-SLM and *E. coli* pellet after 24 h incubation in solvents. CFU count of pellets were corrected for their dry weight. Hex: hexane; $CHCl_3$: chloroform; EtOAc: ethyl acetate; ACN: acetonitrile, EtOH: absolute ethanol; MeOH: methanol; DMF: dimethylformamide. (B) Chart shows miscibility and immiscibility of organic solvents in water. (C) Normalized weights of EC-SLMs before and after 24 h incubation in solvents.
Figure 24B:
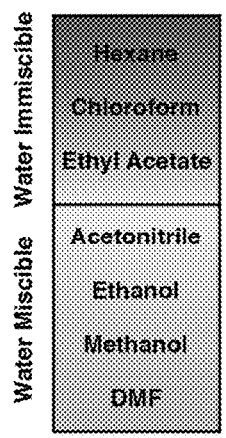
Figure 24C:
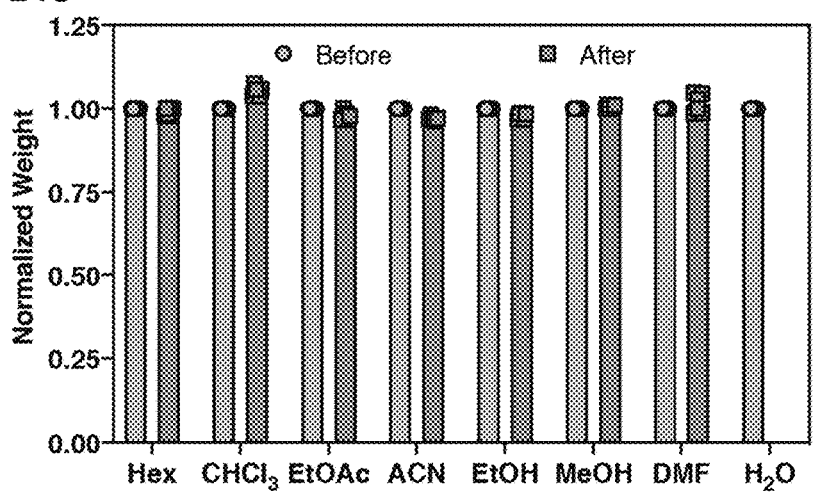
Figure 24D:
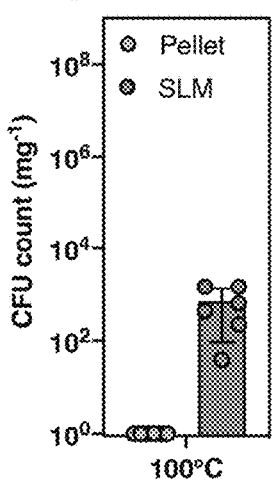
FIG. 24(D) shows the CFU count of EC-SLM and *E. coli* pellet after incubation at 100° C. for 1 h.
Figure 25:
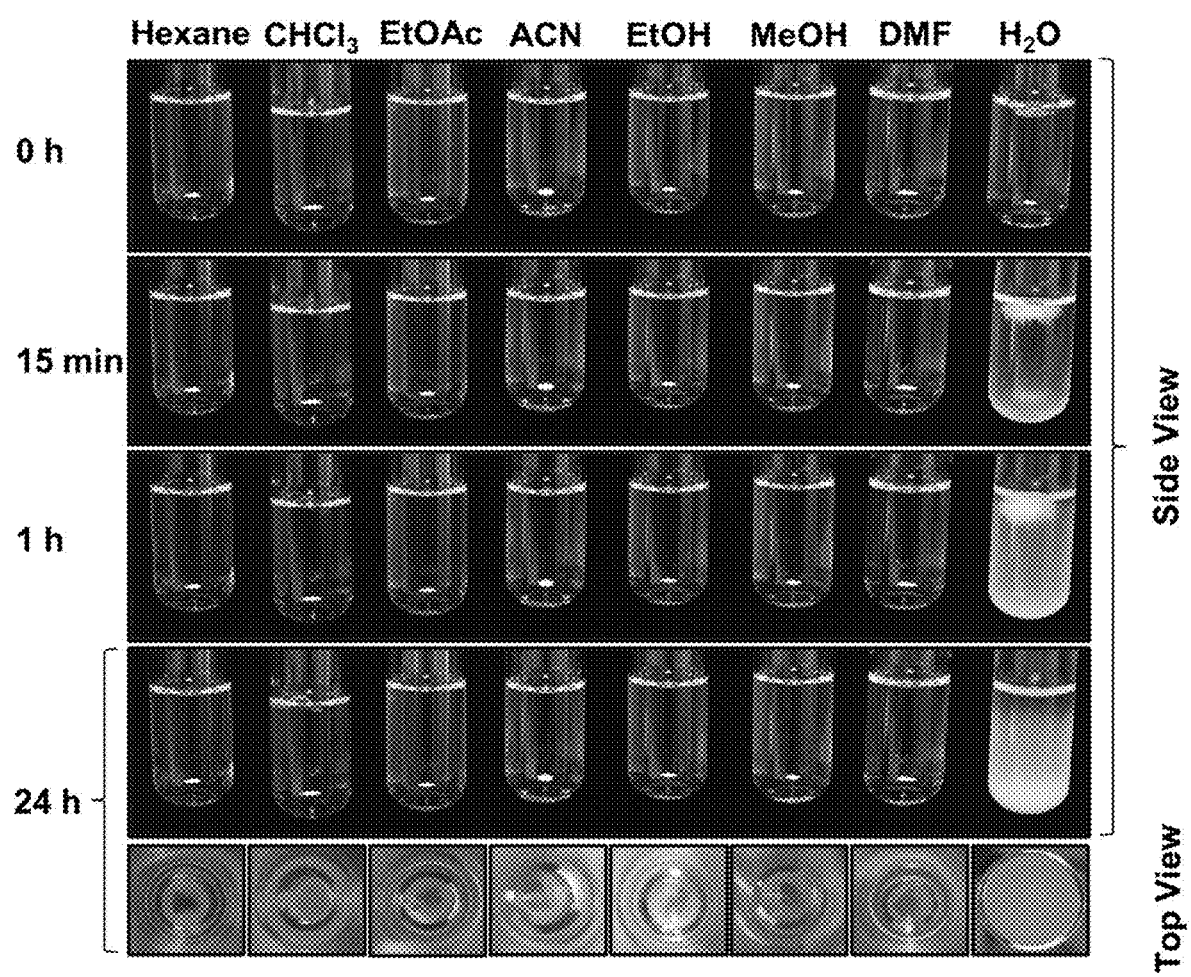
FIG. 25 shows optical images of *E. coli* pellet in various solvents. $CHCl_3$: chloroform, EtOAc: ethyl acetate, ACN: acetonitrile, EtOH: absolute ethanol, MeOH: methanol, DMF: dimethylformamide.

During the fabrication of SLMs, it was learned that PVDF membrane can be removed by gently wiping with DMF solvent. It was also noticed that EC-SLM did not disperse even when submerged in DMF. EC-SLM was then incubated in different solvents viz., hexane, chloroform, ethyl acetate, acetonitrile, absolute ethanol, methanol, DMF and milli-Q water (FIG. 23). Notably, EC-SLM dispersed only in water and not in any other solvents, whose polarity index spans the entire spectrum. After 24 h of incubation in solvents, they were subjected to CFU analysis and greater than $10^6$ $mg^{-1}$ of CFU count was found in all solvents, except chloroform and methanol, in which all cells in the SLM were dead (FIG. 24A). When repeated using the cell pellet instead, the CFU analysis with *E. coli* showed that the cells were dead in all solvents, except for hexane and milli-Q water (FIG. 25). The latter can be attributed to hexane's non-polarity that phase-separates the cell pellet. While in milli-Q water the cells settle at the bottom of the test tube and create an intermediate phase, most likely comprising some lysed cells (FIG. 25). Notably, EC-SLM is stable in both water-miscible and -immiscible organic solvents (FIG. 24B). EC-SLM showed no significant weight loss after the 24 h incubation in solvents, which further supports their stability. The robustness of EC-SLM was also tested by incubating at 100° C. for 1 h and a mean CFU count of over 700 $mg^{-1}$ was observed. These robust characteristics of EC-SLM may be due to a protective outer layer formed from the lysed *E. coli* cells, as seen in FIG. 10D.

Example 8: Mechanical Landscape of SLMs

Figure 26A:
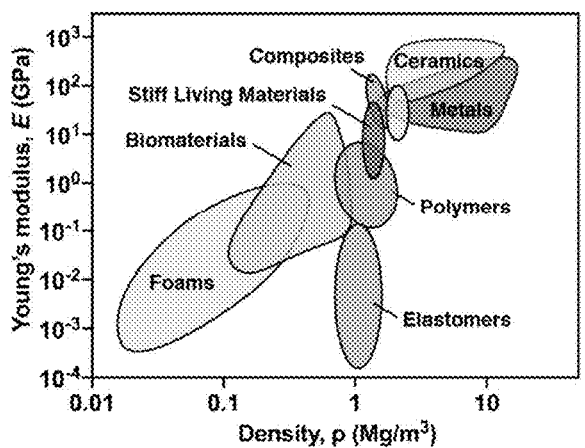
FIGS. 26(A)-26(D) show the mechanical and compositional landscape of SLMs. Ashby plot of (A) Young's modulus verses density, (B) Specific modulus verses specific strength and (C) Young's modulus verses strength, for various classes of materials and SLMs. SWNT: Single-wall carbon nanotube; LDPE: low density polyethylene; HDPE: high density polyethylene, PTFE: polytetrafluoroethylene. (D) Voronoi tree diagram shows the relative amounts of the components present in the dry *E. coli* cell.
Figure 26B:
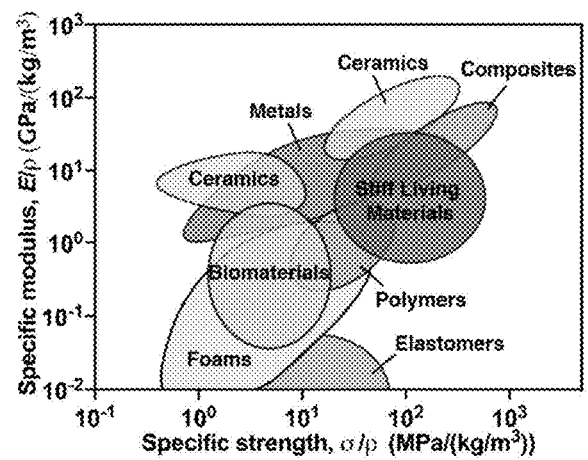
Figure 26C:
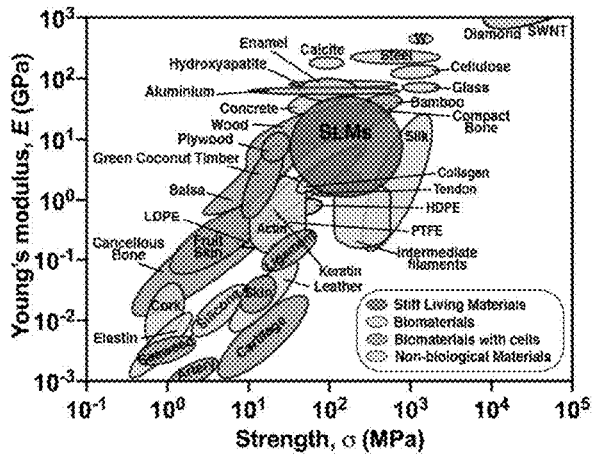

Based on the nanoindentation studies, it is evident that SLMs are both stiff and hard. To put things into perspective, a comparison of the mechanical properties of SLMs to other biomaterials and various types of human-made materials—metals, polymers, composites, ceramics, elastomers and foams is provided. Material properties charts, commonly known as Ashby plots, are presented in FIG. 26A, depicting the plot of Young's modulus, E and density, p, for SLMs and other classes of materials, e.g., metals, polymers, composites, ceramics, elastomers, foams and biomaterials.(31) The SLMs are both light and stiff, which are comparable to biomaterials, polymers and composites. The yield strength, $\sigma_y$ (estimated using the relation $\sigma_y=H/3$) of SLMs was also obtained, which was found to be about 60-800 MPa.(32, 33) In FIG. 26B, the Ashby plot of specific modulus (ratio of E and ρ) and specific strength (ratio of $\sigma_y$ and p) is shown, which indicates that the specific properties of SLMs are comparable to metals and ceramics, due to their low density. (31) Further, provided herein are specific examples of materials that are categorized into biomaterials (e.g. silk, collagen, cellulose etc.), biomaterials with cells (e.g. wood, skin, ligament etc.), non-biological materials (e.g. steel, glass, concrete, plastics etc.) and SLMs in an Ashby plot of E and strength, σ, in FIG. 26C.(31, 34) Notably, the stiffness and strength of SLMs are superior to actin, balsa, cancellous bone, skin and plastics amongst others, and they are comparable to structural materials such as silk, collagen, wood and concrete.

Example 9: Discussion

Microbial cells have been subjected to desiccation under various environmental constraints over millions of years, which has enabled them to develop tolerance to different levels.(35) Xerotolerance of microbes has been studied and widely used (e.g. dry yeast) for nearly a century that has provided interesting insights on the molecular, structural, metabolic and physiological adaptations which keep them alive.(36-38) However, these studies were usually carried out in small volumes (e.g. microliters of microbial culture) that focused on either deciphering the mechanisms of xerotolerance or enhancing the survivability of microbes.(37) On the other hand, the large-scale production of dried microbes were mostly formulated in powder form, which often involves additives, emulsifiers etc.(38) In spite of all the above detailed fundamental and technological advancements, microbes have not been exploited earlier to fabricate a stiff living material and couple their biological properties with physicochemical properties.

Figure 26D:
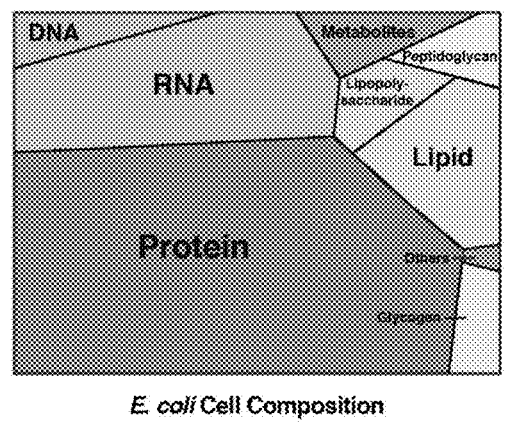

The living cell is a heterogeneous mixture of proteins, nucleic acids, sugars etc. and to comprehend their relative amounts in making the SLM, a Voronoi tree diagram shows the composition of a dry $E.$ $coli$ cell (FIG. 26D, Table 2).(39) Although, it is difficult to ascertain the role of each of these cellular components in the formation of SLM, efforts to fabricate SLM from ethanol treated $E.$ $coli$ cells, wherein the cellular membrane was disrupted, does indicate that the cellular integrity is essential to form a cohesive fragmentation-free material. Accordingly, the biomaterials contemplated herein include those comprising a fully desiccated biomass. Without being bound by theory, the ELMs of the invention (e.g., the SLMs disclosed herein), may be fully desiccated, taking advantage of the assembly, organization, and cellular integrity of the ELMs to fabricate stiff, cohesive, fragmentation-free material that do not comprise living cells.

The latter-type disintegration approaches may help to understand the roles of components, but it has limited scope for the goal of incorporating life-like properties in materials. On the other hand, the various xerotolerance mechanisms (e.g. production of trehalose, extracellular polymeric substances, hydrophilins etc.) are expected to have a significant impact on the self-assembly and survival of cells in SLMs. (36-38, 40) Accordingly, the SLMs disclosed herein may comprise engineered microbes with enhanced or exogenous xerotolerance mechanisms which may include, without limitation and solely for the purpose of exemplification, modified, enhanced or exogenous production of trehalose, extracellular polymeric substances, hydrophilins, and the like as are known in the art (36-38, 40).

TABLE 2

Percentage dry weight of various components in $E.$ $coli$ cell.

| Component | Dry Weight (%) |
| --- | --- |
| Protein | 55 |
| RNA | 20 |
| DNA | 3 |
| Lipid | 9 |
| Lipopolysaccharide | 3 |
| Peptidoglycan | 3 |
| Glycogen | 3 |
| Metabolites | 3 |
| Others | 1 |

Unlike the naturally occurring structural biomaterials (e.g., silk, collagen, bone, wood) that are optimized over million years of evolution for specific mechanical properties, it is remarkable to find that soft and dynamic entities like living cells can also result in similar stiffness and strength. It should be noted that the living cells in wood and bone are embedded in customized structural materials like cellulose, lignin, collagen and hydroxyapatite, whereas in SLMs, the lysed cells and the cellular components produced due to desiccation-induced stress, contribute to their mechanical stiffness.

REFERENCES CITED

1. S. L. Sass, *The Substance of Civilization: Materials and Human History from the Stone Age to the Age of Silicon.* (Arcade Publishing, 2011).
2. Toward the Circular Economy. *Ellen MacArthur Foundation and McKinsey & Company*, (2013).
3. J. M. Benvus, *Biomimicry: Innovation Inspired by Nature.* (Harper Perennial, 2002).
4. U. G. Wegst, H. Bai, E. Saiz, A. P. Tomsia, R. O. Ritchie, Bioinspired structural materials. *Nat Mater* 14, 23-36 (2015).
5. M. A. Meyers, J. McKittrick, P. Y. Chen, Structural biological materials: critical mechanics-materials connections. *Science* 339, 773-779 (2013).
6. F. G. Omenetto, D. L. Kaplan, New opportunities for an ancient material. *Science* 329, 528-531 (2010).
7. A. S. Khalil, J. J. Collins, Synthetic biology: applications come of age. *Nat Rev Genet* 11, 367-379 (2010).
8. P. Q. Nguyen, N. D. Courchesne, A. Duraj-Thatte, P. Praveschotinunt, N. S. Joshi, Engineered Living Materials: Prospects and Challenges for Using Biological Systems to Direct the Assembly of Smart Materials. *Adv Mater* 30, e1704847 (2018).
9. A. Y. Chen, C. Zhong, T. K. Lu, Engineering living functional materials. *ACS Synth Biol* 4, 8-11 (2015).
10. C. Gilbert, T. Ellis, Biological Engineered Living Materials: Growing Functional Materials with Genetically Programmable Properties. *ACS Synth Biol* 8, 1-15 (2019).
11. R. F. Service, In 'living materials,' microbes are makers. *Science* 367, 841 (2020).
12. P. Q. Nguyen, Z. Botyanszki, P. K. Tay, N. S. Joshi, Programmable biofilm-based materials from engineered curli nanofibres. *Nat Commun* 5, 4945 (2014).
13. A. Y. Chen et al., Synthesis and patterning of tunable multiscale materials with engineered cells. *Nat Mater* 13, 515-523 (2014).
14. A. M. Duraj-Thatte et al., Genetically Programmable Self-Regenerating Bacterial Hydrogels. *Adv Mater* 31, e1901826 (2019).
15. P. Praveschotinunt et al., Engineered $E.$ $coli$ Nissle 1917 for the delivery of matrix-tethered therapeutic domains to the gut. *Nat Commun* 10, 5580 (2019).
16. A. M.-B. Pei Kun R. Tay, Neel S. Joshi, Repurposing bacterial extracellular matrix for selective and differential abstraction of rare earth elements. *Green Chemistry* 20, 3512-3520 (2018).
17. Z. Botyanszki, P. K. Tay, P. Q. Nguyen, M. G. Nussbaumer, N. S. Joshi, Engineered catalytic biofilms: Site-specific enzyme immobilization onto $E.$ $coli$ curli nanofibers. *Biotechnol Bioeng* 112, 2016-2024 (2015).
18. N.-M. Dorval Courchesne et al., Biomimetic engineering of conductive curli protein films. *Nanotechnology* 29, 454002 (2018).
19. U. O. Seker, A. Y. Chen, R. J. Citorik, T. K. Lu, Synthetic Biogenesis of Bacterial Amyloid Nanomaterials with Tunable Inorganic-Organic Interfaces and Electrical Conductivity. *ACS Synth Biol* 6, 266-275 (2017).

20. H. M. Jensen et al., Engineering of a synthetic electron conduit in living cells. *Proc Natl Acad Sci USA* 107, 19213-19218 (2010).
21. M. Charrier et al., Engineering the S-Layer of *Caulobacter crescentus* as a Foundation for Stable, High-Density, 2D Living Materials. *ACS Synth Biol* 8, 181-190 (2019).
22. C. Zhong et al., Strong underwater adhesives made by self-assembling multi-protein nanofibres. *Nat Nanotechnol* 9, 858-866 (2014).
23. Y. Cao et al., Programmable assembly of pressure sensors using pattern-forming bacteria. *Nat Biotechnol* 35, 1087-1093 (2017).
24. L. M. Gonzalez, N. Mukhitov, C. A. Voigt, Resilient living materials built by printing bacterial spores. *Nat Chem Biol* 16, 126-133 (2020).
25. J. Huang et al., Programmable and printable *Bacillus subtilis* biofilms as engineered living materials. *Nat Chem Biol* 15, 34-41 (2019).
26. X. Liu et al., 3D Printing of Living Responsive Materials and Devices. *Adv Mater* 30, (2018).
27. X. Liu et al., Stretchable living materials and devices with hydrogel-elastomer hybrids hosting programmed cells. *Proc Natl Acad Sci USA* 114, 2200-2205 (2017).
28. A. M. Duraj-Thatte A, Dorval Courchesne N M, Cannici G, Sánchez-Ferrer A, Frank B P, van't Hag L, Fairbrother D H, Mezzenga R, Joshi N S, Water-Processable, Biodegradable and Coatable Aquaplastic from Engineered Microbial Biofilms. *Nature Chemical Biology under revision*, (2020).
29. S. Varughese, M. S. Kiran, U. Ramamurty, G. R. Desiraju, Nanoindentation in crystal engineering: quantifying mechanical properties of molecular crystals. *Angew Chem Int Ed Engl* 52, 2701-2712 (2013).
30. J.-i. J. Upadrasta Ramamurty, Nanoindentation for probing the mechanical behavior of molecular crystals—a review of the technique and how to use it. *CrystEngComm* 1, 12-23 (2014).
31. M. B. Avinash, D. Raut, M. K. Mishra, U. Ramamurty, T. Govindaraju, Bioinspired Reductionistic Peptide Engineering for Exceptional Mechanical Properties. *Sci Rep* 5, 16070 (2015).
32. P. Zhang, S. X. Li, Z. F. Zhang, General relationship between strength and hardness. *Materials Science and Engineering: A* 529, 62-73 (2011).
33. M. F. Ashby, *Materials Selection in Mechanical Design*. (Butterworth-Heinemann, 2005).
34. T. P. Knowles, M. J. Buehler, Nanomechanics of functional and pathological amyloid materials. *Nat Nanotechnol* 6, 469-479 (2011).
35. D. A. Wharton, *Life at the limits: organisms in extreme environments*. (Cambridge University Press, Cambridge, UK; New York, 2002), pp. xi, 307 p.
36. P. H. Lebre, P. De Maayer, D. A. Cowan, Xerotolerant bacteria: surviving through a dry spell. *Nat Rev Microbiol* 15, 285-296 (2017).
37. M. Potts, Desiccation tolerance of prokaryotes. *Microbiol Rev* 58, 755-805 (1994).
38. G. Reed, T. W. Nagodawithana, *Yeast technology*. (Van Nostrand Reinhold, New York, ed. 2nd, 1991), pp. ix, 454 p.
39. R. Milo, R. Phillips, N. Orme, *Cell biology by the numbers*. (Garland Science, New York, N.Y., 2016), pp. xlii, 356 pages.
40. M. Potts, S. M. Slaughter, F. U. Hunneke, J. F. Garst, R. F. Helm, Desiccation tolerance of prokaryotes: application of principles to human cells. *Integr Comp Biol* 45, 800-809 (2005).

What is claimed is:

1. An engineered living material (ELM), comprising a plurality of microbial cells without the incorporation of any structural biopolymers, wherein the ELM has a Young's modulus of at least 5 GPa, and the microbial cells are *Escherichia coli* strain PQN4.

2. The ELM of claim 1, wherein the ELM has a hardness of 0.2 GPa to 2.4 GPa, or a yield strength of 60-800 MPa.

3. The ELM of claim 1, wherein the microbial cells are xerotolerant, engineered to have enhanced xerotolerance, or xerophilic.

4. The ELM of claim 1, wherein the microbial cells are extremophilic.

5. The ELM of claim 1, comprising an outer surface of lysed or desiccated microbial cells; and a core of living microbial cells.

6. The ELM of claim 5, wherein said ELM is capable of self-regeneration.

7. The ELM of claim 5, wherein the biomass of the ELM is fully desiccated.

8. The ELM of claim 1, wherein said ELM is resistant to organic solvents.

9. The ELM of claim 2, wherein the biomass of the ELM is fully desiccated.

10. The ELM of claim 2, wherein the microbial cells are xerotolerant, engineered to have enhanced xerotolerance, or xerophilic.

11. The ELM of claim 2, wherein the microbial cells are extremophilic.

12. The ELM of claim 2, wherein said ELM is resistant to organic solvents.

13. The ELM of claim 7, wherein the microbial cells are xerotolerant, engineered to have enhanced xerotolerance, or xerophilic.

14. The ELM of claim 7, wherein the microbial cells are extremophilic.

15. The ELM of claim 7, wherein said ELM is resistant to organic solvents.

* * * * *